US011105802B2

(12) United States Patent
Grewal et al.

(10) Patent No.: US 11,105,802 B2
(45) Date of Patent: Aug. 31, 2021

(54) CELL-FREE BIOFRAGMENT COMPOSITIONS AND RELATED SYSTEMS, DEVICES, AND METHODS

(71) Applicants: The University of Queensland, St. Lucia (AU); Seattle Children's Hospital, Seattle, WA (US)

(72) Inventors: Yadveer Grewal, Logan City (AU); Gerard A. Cangelosi, Seattle, WA (US); Muhammad J. A. Shiddiky, Saint Lucia (AU); Matt Trau, Balmoral (AU)

(73) Assignees: SEATTLE CHILDREN'S HOSPITAL, Seattle, WA (US); The University of Queensland, St. Lucia (AU)

( * ) Notice: Subject to any disclaimer, the term of this patent is extended or adjusted under 35 U.S.C. 154(b) by 16 days.

(21) Appl. No.: 14/650,851

(22) PCT Filed: Dec. 10, 2013

(86) PCT No.: PCT/US2013/074149
§ 371 (c)(1),
(2) Date: Jun. 9, 2015

(87) PCT Pub. No.: WO2014/093357
PCT Pub. Date: Jun. 19, 2014

(65) Prior Publication Data

US 2015/0377880 A1 Dec. 31, 2015

Related U.S. Application Data

(60) Provisional application No. 61/735,180, filed on Dec. 10, 2012.

(51) Int. Cl.
*G01N 33/566* (2006.01)
*G01N 33/543* (2006.01)
*G01N 33/569* (2006.01)

(52) U.S. Cl.
CPC ....... *G01N 33/566* (2013.01); *G01N 33/5432* (2013.01); *G01N 33/5438* (2013.01); *G01N 33/56911* (2013.01); *G01N 33/56961* (2013.01); *G01N 33/56966* (2013.01); *G01N 33/56983* (2013.01)

(58) Field of Classification Search
None
See application file for complete search history.

(56) References Cited

U.S. PATENT DOCUMENTS

| | | | | |
|---|---|---|---|---|
| 6,300,065 B1 | 10/2001 | Kieke et al. | | |
| 2003/0166099 A1* | 9/2003 | Sabbadini | C12N 15/1037 | 506/10 |
| 2006/0003387 A1* | 1/2006 | Peelle | C12N 15/1037 | 435/7.2 |
| 2007/0224208 A1* | 9/2007 | Guo | A61K 39/0011 | 424/184.1 |
| 2008/0003239 A1* | 1/2008 | Duke | A61K 39/145 | 424/206.1 |
| 2008/0171059 A1* | 7/2008 | Howland | A61K 39/0011 | 424/185.1 |
| 2010/0168390 A1* | 7/2010 | Brix | A61K 47/4823 | 530/350 |
| 2011/0086768 A1* | 4/2011 | Turner | C07K 14/705 | 506/9 |
| 2011/0275535 A1 | 11/2011 | Loew | | |

FOREIGN PATENT DOCUMENTS

| | | | | |
|---|---|---|---|---|
| WO | 2004/044004 A2 | 5/2004 | | |
| WO | WO-2011032119 A1 * | 3/2011 | A61K 39/39541 | |
| WO | 2012/159075 A1 | 11/2012 | | |

OTHER PUBLICATIONS

Bryan, C.M., et al., "High-Throughput Protein Production and Purification at the Seattle Structural Genomics Center or Infectious Disease," Acta Crystallographica Section F Structural Biology and Crystallization Communications 57(9):1010-1014, Sep. 2011.
Georgiou, G. et al., "Display of Heterologous Proteins on the Surface of Microorganisms: From the Screening of combinatorial Libraries to Live Recombinant Vaccines," Nature Biotechnology 15(1):29-34, Jan. 1997.
Gray, S.A., et al., "Flow Cytometry-Based Methods for Assessing Soluble scFv Activities and Detecting Antigens in Solution," Biotechnology Bioengineering 105(5):973-981, Apr. 2010.
Gray, S.A., et al., "Toward Low-Cost Affinity Reagents: Lyophilized Yeast-scFv Probes Specific for Pathogen Antigens," PLoS One 7(2):e32042, Feb. 2012.
Grewal, Y.S., et al., "Label-Free Electrochemical Detection of an Entamoeba histolytica Antigen Using Cell-Free Yeast-scFv Probes," Chemical Communications 49(15):1551-1553, Feb. 2013.
He, M. and F. Khan, "Ribosome Display: Next-Generation Display Technologies for Production of Antibodies in vitro," Expert Review of Proteomics 2(3):421-430, Jun. 2005.
Ho, M., et al., "Isolation of Anti-CD22 Fv with High Affinity by Fv Display on Human Cells," PNAS 103(25):9637-9642, Jun. 2006.

(Continued)

*Primary Examiner* — Ellen J Marcsisin
(74) *Attorney, Agent, or Firm* — Christensen O'Connor Johnson Kindness PLLC

(57) ABSTRACT

The present disclosure relates to biofragment compositions that comprise bioparticle fragments and at least one heterologous antigen-binding molecule. In some embodiments, the biofragment is typically derived from a larger, intact bioparticle that express the at least one heterologous antigen-binding molecule at the surface, and the biofragment has increased solubility to facilitate assays for antigen detection. The disclosure also relates the related methods of using and making the biofragment compositions, as well as systems and devices implementing the biofragment compositions. In some embodiments, the related methods, systems and devices do not require additional detection reagents, such as animal derived detection antibodies.

19 Claims, 9 Drawing Sheets

(56) References Cited

OTHER PUBLICATIONS

Kanter, G., et al., "Cell-Free Production of scFv Fusion Proteins: An Efficient Approach for Personalized Lymphoma Vaccines," Blood 109(8):3393-3399, Apr. 2007.
Katz, E., and I. Willner, "Probing Biomolecular Interactions at Conductive and Semiconductive Surfaces by Impedance Spectroscopy: Routes to Impedimetric Immunosensors, DNA-Sensors, and Enzyme Biosensors," Electroanalysis 15(11):913-947, 2003.
Kierny, M.R., et al., "Detection of Bomarkers Using Recombinant Antibodies Coupled to Nanostructured Platforms," Nano Reviews 3:1-24, Jul. 2012.
Kim, J.Y., et al., "Engineered Bacterial Outer Membrane Vesicles with Enhanced Functionality," Journal of Molecular Biology 380(1):51-66, Jun. 2008.
Stacey, R., et al., "Structural Genomics of Infectious Disease Drug Targets: the SSGCID," Acta Crystallographica Section F Structural Biology and Crystallization Communications 67(9):979-984, Sep. 2011.
Wsowicz, M., et al., "Immunosensor Incorporating Anti-His (C-term) IgG F(ab') Fragments Attached to Gold Nanorods for Detection of His-Tagged Proteins in Culture Medium," Sensors 10(6):5409-5424, 2010.
Zhou, M., and D. Shaojun, "Bioelectrochemical Interface Engineering: Toward the Fabrication of Electrochemical Biosensors, Biofuel Cells, and Self-Powered Logic Biosensors," Accounts of Chemical Research 44(11):1232-1243, Nov. 2011.
Written Opinion and International Search Report dated Mar. 3, 2014, issued in corresponding International Application No. PCT/US2013/074149, filed Dec. 10, 2013, 14 pages.
Extended European Search Report dated May 30, 2016, issued in corresponding European Application No. EP 13863100.7, filed Dec. 10, 2013, 9 pages.
Australian Examination Report No. 1 dated Aug. 16, 2018, issued in corresponding Australian Application No. 2013359469, filed Dec. 10, 2013, 4 pages.
Communication Pursuant to Article 94(3) EPC dated Jan. 25, 2018, issued in corresponding European Application No. 13863100.7, filed Dec. 10, 2013, 5 pages.

* cited by examiner

CELL-FREE BIOFRAGMENT COMPOSITIONS AND RELATED SYSTEMS, DEVICES, AND METHODS

CROSS-REFERENCE TO RELATED APPLICATION

CROSS-REFERENCES TO RELATED APPLICATIONS

This application is a U.S. National Stage of PCT/US2013/074149, filed Dec. 10, 2013, which claims the benefit of Provisional Application No. 61/735,180, filed Dec. 10, 2012, the entire disclosures of said applications are hereby incorporated by reference.

STATEMENT OF GOVERNMENT LICENSE RIGHTS

This invention was made with Government support under AI082186 awarded by the National Institutes of Health. The Government has certain rights in the invention.

BACKGROUND

Affinity reagents that bind to specific antigens of interest are critical tools in biomedical research, biomarker discovery, and diagnostic testing. Generation of monoclonal antibodies (MAbs) by traditional methods, typically by the mouse hybridoma route, is a significant bottleneck in biomedical research and development. MAbs in diagnostic tests often require significant optimization before being usable for diagnostic assays, and licensing costs can exceed all other test costs combined. Cheaper and more available affinity reagents would greatly facilitate biomedical research, empower developers of new diagnostic tests, and facilitate development and use of inexpensive and sensitive assays, testing devices and testing systems.

Recombinant antibody-like molecules such as single-chain Fragment variable (scFv) and fragment antigen binding (Fab) are potentially appealing alternatives to MAbs. Libraries of these molecules have been displayed on the surfaces of organisms including *Escherichia coli*, phages, yeast, and on ribosomes. Although these methods have existed for many years, few such fragments have proven useful as molecular probes in diagnostic tests. Methods for rapidly selecting antigen-binding yeast-displayed scFv clones were described nearly ten years ago. For example, yeast display libraries can be made to express scFv on the surface of *Saccharomyces cerevisiae* cells. Using a combination of magnetic bead enrichment and fluorescent-activated cell sorting (FACS), yeast clones that bind specifically to antigens of interest can be selected from naïve libraries in 2-3 weeks. This selection process is much faster and less expensive than the mouse hybridoma route. However, scFv selected by this method rarely perform well when secreted into solution. Like natural antibodies, yeast-displayed scFv are products of selection, in this case for activity in the environment of a yeast cell surface. Hence, yeast-displayed scFv tend to perform poorly in other environments, especially when secreted. Although functional soluble scFv have been reported, in practice the great majority of scFv culled from yeast display libraries have exhibited unsatisfactory activity in standard immunoassay formats, thus requiring additional rounds of optimization. Therefore, the reliable and efficient production of scFv for use as effective affinity reagents remains unpredictable.

Despite the advances in the art regarding production of affinity reagents, such as monoclonal antibodies and antibody-like molecules, a need remains for fast and cost-effective production of versatile reagents useful for reliable detection of antigens of interest. The invention set forth in this disclosure addresses this need and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present invention provides a biofragment composition for selectively binding an antigen of interest in a sample. The biofragment composition comprises a bioparticle fragment displaying at least one heterologous antigen-binding molecule, wherein the at least one heterologous antigen-binding molecule is capable of specifically binding the antigen of interest.

In some embodiments, the bioparticle of the composition is a cell, a cellular organelle, or a virus. In some embodiments, the cell is selected from the group consisting of a yeast, bacterium, plant, or animal cell. In some embodiments, the yeast is from the genus *Saccharomyces* or *Pichia*.

In some embodiments, the heterologous antigen-binding molecule of the biofragment composition is an antibody-like molecule or a T cell receptor (TCR). In some embodiments, the antigen-binding molecule comprises an antigen-binding fragment of an antibody or TCR. In some embodiments, the antibody-like molecule is a single-chain antibody, a bispecific antibody, an Fab fragment, or an $F(ab)_2$ fragment. In some embodiments, the single-chain antibody is a single-chain variable fragment (scFv), single-chain Fab fragment (scFab), $V_HH$ fragment, $V_{NAR}$, or Nanobody®.

In some embodiments, the bioparticle fragment displaying at least one heterologous antigen-binding molecule is substantially isolated from bioparticle fragments not displaying the at least one heterologous antigen-binding molecule. In some embodiments, the bioparticle fragment is less than about 1 μm at its greatest dimension. In some embodiments, the bioparticle fragment is produced by disruption of the bioparticle surface. In some embodiments, the bioparticle fragment is derived from a larger bioparticle, wherein the bioparticle fragment has increased solubility in aqueous assay conditions. In some embodiments, the at least one heterologous antigen-binding molecule is attached to the bioparticle surface prior to disruption of the surface by inducing expression and translocation of the molecule to, or assembly of the molecule on, the interior or exterior bioparticle surface.

In another aspect, the disclosure provides a method of detecting the presence of an antigen of interest in a biological sample. The method comprises contacting a biological sample with the biofragment composition as described herein under conditions sufficient to permit the binding of the composition with an antigen of interest, and detecting the binding of the biofragment composition to the antigen of interest.

In some embodiments, the method further comprises immobilizing the biofragment composition. In some embodiments, the method further comprises contacting the biological sample with a detection reagent that binds to the antigen of interest. In some embodiments, the method further comprises contacting the biological sample with a detectably-labeled reporter reagent and separating the unbound reporter from the biofragment composition. In some embodiments, binding of the antigen of interest to the biofragment composition is detected using an antibody sandwich flow cytometric assay, cell bioprobe immunofluorescence microscopy, an ELISA-like assay, or a competitive inhibition assay. In some embodiments, the biofragment composition is immobilized, directly or indirectly, to a conductive or semi-conductive electrode surface. In some embodiments, the method further comprises providing an electroactive molecule and measuring the electron transfer resistance at the electrode surface, wherein binding of the antigen of interest to the biofragment composition is detected by a change in the electron transfer resistance as compared to the electron transfer resistance when the antigen of interest is not present. In some embodiments, the biological sample is selected from the group consisting of blood, urine, sputum, mucus, saliva, cerebral spinal fluid, tissues, stool, nutrient sources, or processed derivatives thereof.

In another aspect, the disclosure provides a method of detecting the presence of an antigen of interest in a biological sample. The method comprises 1) contacting a biological sample with a capture reagent that binds to the antigen of interest; and 2) contacting the biological sample with a detection reagent under conditions sufficient to permit the binding of the detection reagent with an antigen of interest, wherein the detection reagent comprises the biofragment composition described herein. In some embodiments, the detection reagent further comprises a detectable label. In some embodiments, the method further comprises contacting the biological sample with a detectably-labeled reporter agent that specifically binds to the detection reagent, and removing the unbound reporter agent.

In another aspect, the disclosure provides a method of detecting the presence of an antigen of interest in a biological sample. The method comprises 1) contacting a biological sample to the biofragment composition described herein under conditions sufficient to permit the binding of the antigen of interest to the biofragment composition, wherein the biofragment composition is immobilized, directly or indirectly, to a conductive or semi-conductive electrode surface; and 2) measuring the electron transfer resistance at the electrode surface in the presence of an electroactive molecule, wherein binding of the antigen of interest to the biofragment composition is detected by a change in the electron transfer resistance as compared to the electron transfer resistance when the antigen of interest is not present.

In some embodiments, the electroactive molecule is a redox probe. In some embodiments, the redox probe is $[Fe(CN)_6]^{3-/4-}$.

In some embodiments, the biofragment composition is immobilized indirectly to the electrode surface by one or more intervening tether constructs. In some embodiments, the method further comprises the step of immobilizing the biofragment composition to the electrode surface. In some embodiments, the immobilizing step comprises: a) attaching an anchor construct to the electrode, b) immobilizing an epitope-tag binding molecule to the anchor construct, and c) contacting the epitope-tag binding molecule with the biofragment composition, wherein the biofragment composition comprises heterologous antigen-binding molecule with an epitope tag. In some embodiments, step "c)" comprises: i) disrupting the surface of one or more bioparticles that have at least one attached heterologous antigen-binding molecule attached thereto to produce a plurality of bioparticle surface fragments, ii) contacting the epitope-tag binding molecule with the plurality of bioparticle fragments to the epitope-tag binding molecule, and iii) removing the bioparticle surface fragments that remain unbound to the immobilized epitope-tag binding molecule. In some embodiments, the method further comprises optionally rinsing the electrode surface after one or more of steps a), b), and c).

In some embodiments, the anchor construct is a protein, organic or inorganic molecule. In some embodiments, the epitope tag is any epitope, such as c-myc, HA, FLAG-tag, GST, 6HIS, VSVg, V5, HSV, AU1, and the like.

In some embodiments, binding of the antigen of interest to the biofragment composition is detected by an increase in the electron transfer resistance as compared to the electron transfer resistance when the antigen of interest is not present.

In another aspect, the disclosure provides an antigen detection system. The system comprises the biofragment composition as described herein immobilized directly or indirectly to a conductive or semi-conductive electrode surface, also described herein. The system also comprises an electroactive molecule, and a device to monitor electric current, electric potential, and/or electric impedance, such as a potentiostat or a galvanostat, and the like. In some embodiments, the biofragment composition is immobilized indirectly to the electrode surface by one or more intervening tether constructs. In some embodiments, the one intervening tether construct is an epitope-tag binding molecule that binds to an epitope tag present in the heterologous antigen-binding molecule of the biofragment composition.

In another aspect, the disclosure provides a device that implements the system and/or incorporates the biofragment composition, as described herein, which can be useful, for example, for the point of care detection of antigens of interest from a biological sample.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
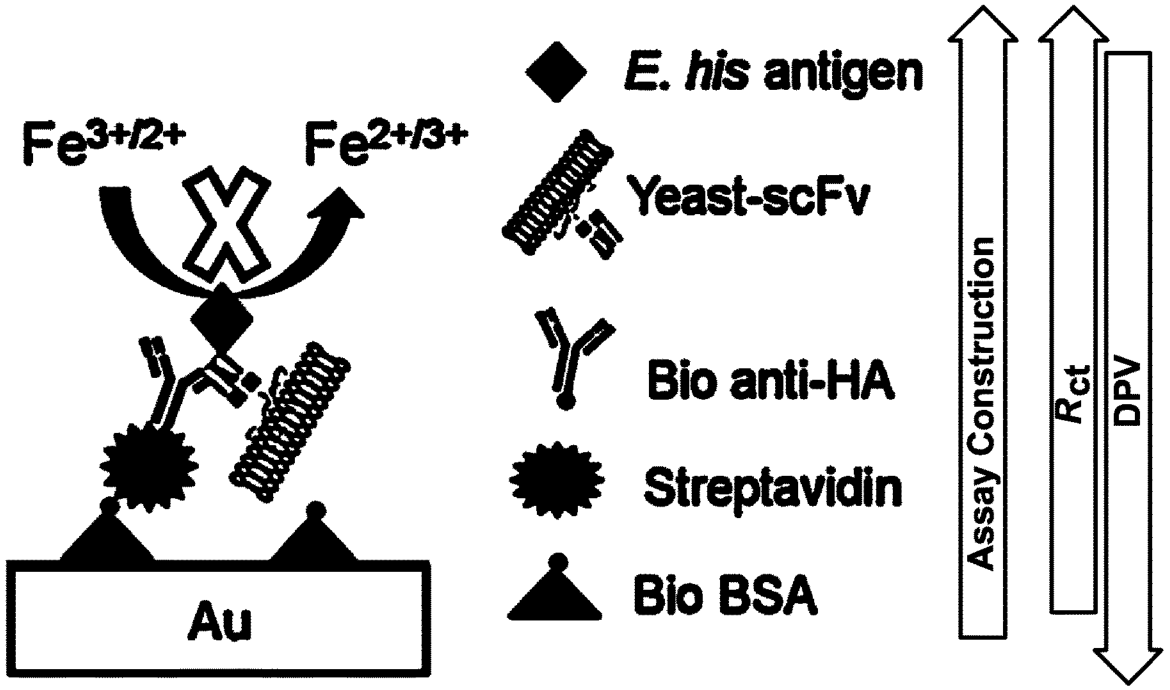
FIG. 1A is a general schematic illustration of a label-free protein detection system based on faradaic electrochemical impedance spectroscopy (F-EIS). Illustrated in the scheme are *E. histolytica* proteins complexed with surface-attached yeast-scFv biofragments, which hinder the interfacial electron transfer reaction of $[Fe(CN)_6]^{3-/4-}$.

Disclosed are materials, compositions, and components that can be used for, can be used in conjunction with, can be used in preparation for, or are products of the disclosed methods, compositions, and related systems and devices. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

As used in this specification and the appended claims, the singular forms "a," "an," and "the" include plural references unless the context clearly dictates otherwise. Thus, for example, references to "the method" includes one or more methods, and/or steps of the type described herein and/or which will become apparent to those persons skilled in the art upon reading this disclosure and so forth. The use of the term "or" in the claims is used to mean "and/or" unless explicitly indicated to refer to alternatives only or the alternatives are mutually exclusive, although the disclosure supports a definition that refers to only alternatives and "and/or." As used in this specification, the term "about" refers to a range of slight variation, such as 10%, above or below the stated figure.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Unless specifically defined herein, all terms used herein have the same meaning as they would to one skilled in the art of the present invention. Practitioners are particularly directed to Sambrook, et al., *Molecular Cloning: A Laboratory Manual,* 3d ed., Cold Spring Harbor Press, Plainsview, N.Y. (2000) and Ausubel, et al., *Current Protocols in Molecular Biology* (Supplement 47), John Wiley & Sons, New York (1999), which are incorporated herein by reference, for definitions and terms of the art. Additionally, all other references cited herein are hereby expressly incorporated by reference in their entireties.

One solution to problems associated with the generation of monoclonal antibodies and antibody-like molecules for affinity reagents is to forgo the attempt to generate soluble scFv and instead use the yeast-displayed scFv (whole-cell yeast-scFv) directly as detection reagents. Affinity reagents composed of lyophilized whole yeast cells with displayed scFv (whole-cell yeast scFv) have been shown to be viable, cheap and quick alternatives to generating mAbs or soluble scFv for use in Immunoassays (Gray, S. A., et al, "Toward Low-Cost Affinity Reagents: Lyophilized Yeast-scFv Probes Specific for Pathogen Antigens," *PLoS ONE* 7: e32042 (2012); see also WO 2012/159075; each of which are hereby incorporated by reference in their entireties). Whole-cell yeast scFv are robust and renewable reagents that can be produced in vast quantities at low cost. However, these whole-cell reagents are insoluble and too large for many diagnostic applications. Moreover, they require the use of labeled polyclonal antibodies to detect antigen binding to the yeast scFv particles (Gray et al, 2012).

The present invention, which overcomes the limitations of the art as described above, not only provides sensitive cell-free scFv affinity reagents, but also provides an affinity reagent system that does not require labeled, animal derived detection antibodies. As described in more detail below, the inventors generated cell-free scFv affinity reagents using fragmentation of whole-cell yeast scFv cells, followed by mechanical and affinity based purification of smaller, soluble cell wall fragments bearing displayed scFv. Moreover, an electrochemical (EC) approach was used to detect antigen binding to cell free yeast scFv, without the need for animal derived detection antibodies.

In accordance with the foregoing, in one aspect, the present disclosure provides a biofragment composition for selectively binding an antigen of interest in a sample. The biofragment composition comprises a bioparticle fragment displaying at least one heterologous antigen-binding molecule, wherein the at least one heterologous antigen-binding molecule is capable of specifically binding the antigen of interest.

As used herein, the term "biofragment" is used to refer to any fragment of a bioparticle that contains or displays on its internal or external surface at least one heterologous antigen binding molecule, where the heterologous antigen binding molecule is capable of specifically binding the antigen of interest. In some embodiments, the biofragment is a surface portion of the original bioparticle. Thus, the biofragment is not an intact bioparticle (see below), but rather a bioparticle or portion thereof where the bioparticle surface has been disrupted. In some embodiments, the bioparticle surface is disrupted sufficiently to lose its initial shape or integrity, but remains in a single piece. In other embodiments, the bioparticle surface has been disrupted into multiple, independent pieces such that each resulting biofragment contains less than all of the surface area than the initial intact bioparticle.

As used herein, the term "bioparticle" is used to refer to any particle derived from a biological system while retaining the integrity of heterologous antigen-binding molecules contained or displayed (internally or externally) on the surface structure of the bioparticle. Thus, the term "bioparticle" can encompass intact cells, cellular organelles, viruses, or other biological constructs that can be assembled, propagated, or generated to display on the inner or outer surface at least one heterologous antigen-binding molecule. For any embodiment, there is no requirement that the bioparticle be living or demonstrate metabolic integrity post-lyophilization. However, the bioparticle surface must be amenable to disruption or fragmentation that allows the retention of heterologous antigen-binding molecules contained in, attached to, or displayed on, the resulting surface fragments. In this context, the term "functional" is used to indicate that the heterologous antigen-binding molecule(s) retain the capacity to selectively bind the antigen of interest, while also remaining attached to any bioparticle fragment (i.e., biofragment; see below).

In some embodiments, the bioparticle is a cell. As will be apparent to persons of ordinary skill in the art, the bioparticle can be any cell that can be made to express, attach and/or display a heterologous antigen-binding molecule on its surface and that can retain its attachment and structural integrity upon fragmentation of the bioparticle. In some embodiments, the cell is a microbial cell, such as a yeast or bacterial cell. In alternative embodiments, the cell is a plant or animal cell. In some embodiments, the cells that contain rigid cell walls are selected for use as bioparticles because the rigid cell wall can enhance the fragment integrity after the fragmentation process.

In some embodiments, the bioparticle cell is a yeast cell. Exemplary yeasts include yeast selected from the genera *Saccharomyces* or *Pichia*, for example, *Saccharomyces cerevisiae* or *Pichia pastoralis*. For example, yeast bioparticles have generated by screening libraries of *Saccharomyces cerevisiae* displaying human-derived single-chain variable antibody fragments (scFv) on their surface. However, persons of skill in the art will recognize that the present compositions are not limited to such embodiments, but rather encompass any yeast amenable to display of heterologous antigen-binding molecule on its surface using common recombinant DNA techniques. See, e.g., Sambrook, et al. (2000) or Ausubel, et al. (1999).

In other embodiments, the bioparticle cell is a bacterium. The bacterium can be Gram positive or Gram negative. Exemplary bacteria are selected from the genera *Bacillus* (Gram positive) and *Escherichia* (Gram negative). Specific examples include *Bacillus megaterium* and *Escherichia coli*. Transgenic bacteria have been used to display a library of heterologous polypeptides, including scFv antibodies, which are retained on the surface for subsequent cell sorting. See, e.g., Georgiou, G., et al., "Display of Heterologous Proteins on the Surface of Microorganisms: From the Screening of Combinatorial Libraries to Live Recombinant Vaccines," *Nat. Biotechnol.* 15:29-34, 1997. As above, persons of skill in the art will recognize that the present compositions are not limited to such embodiments, but rather encompass any bacterium amenable to attachment or display of heterologous antigen-binding molecule to its surface using common recombinant DNA techniques. See, e.g., Sambrook, et al. (2000) or Ausubel, et al. (1999).

In yet other embodiments, the bioparticle is a non-microbial cell, such as an animal cell or a plant cell. For example, scFvs have been displayed and isolated from human embryonic kidney 293T (HEK-293T) cells (see, e.g., Ho, M. et al., "Isolation of Anti-CD22 Fv With High Affinity by Fv Display on Human Cells," *Proc. Natl. Acad. Sci. USA* 103:9637-9642, 2006).

In other embodiments, the bioparticle is a cellular organelle. An exemplary organelle is the ribosome, which has been previously used to display large repertoires of antibodies and antibody-like molecules. See, e.g., He, M. and Khan, F., "Ribosome Display: Next-Generation Display Technologies of Antibodies In Vitro," *Expert Rev. Proteomics* 2:421-430, 2005.

In other embodiments, the bioparticle is a virus. An illustrative example is a bacteriophage. Use of bacteriophages to display libraries of exogenous polypeptides has been established. For example, using filamentous M13-derived bacteriophages, many display libraries have been made by expressing the exogenous polypeptides as fusions with the bacteriophage coat protein pIII. As the virus is assembled within the host bacterium, the fusion protein is transported to the bacterial periplasm and incorporated into the phage particle. Additional M13 filamentous proteins that have been utilized for fusion with the exogenous polypeptides include pVI, pVII, pVIII, and pIX. In the context of antibody-like polypeptides, the result is a library of diverse antibody-like polypeptides with intact binding properties linked to the DNA that encodes them, which enables the subsequent selection and propagation of polypeptides exhibiting particular binding properties.

The bioparticle fragment (i.e., biofragment) can be produced by any method commonly known in the art. For example, the bioparticle can be fragmented mechanically, such as with simple mortar and pestle techniques, as described below. Based on the bioparticle, a preliminary treatment step, such as lyophilization or freezing, can be advantageous. Other fragmentation techniques can include sonication, electroporation, and the like. In yet other embodiments, fragmentation can be accomplished chemically, such as by introduction of agents that disrupt external membranes of the bioparticle.

The resulting biofragment is typically smaller than the size of the initial bioparticle. For example, if the initial bioparticle is a cell, for most embodiments the biofragment will likely be less than 3 μm, and in some embodiments less than 1 μm, at the greatest dimension of the biofragment. In some embodiments, the biofragments are between about 1 μm to about 500 μm. In some embodiments, the biofragments are between about 20 μm to about 200 μm. In some embodiments, the biofragments are between about 50 μm to about 100 μm. In yet other embodiments, such as embodiments that are derived from cellular organelles or viruses, the fragments are less than 0.5 μm, less than 0.2 μm, or less than 0.1 μm.

In some embodiments, the biofragments have increased solubility in aqueous assay conditions over the initial bioparticle from which they are derived. For example, as described above, whole-cell yeast-scFv affinity reagents can have low solubility, thus limiting their applicability in various assay conditions. However, as described below in more detail, when the whole-cell yeast-scFv are fragmented, the resulting yeast-scFv biofragments are very soluble and are highly functional in antigen-detection assays. Thus, in some embodiments, the biofragments are soluble or semi-soluble in aqueous solutions. As indicated by the term "semi-soluble", the biofragments do not necessarily have to be completely soluble. However, the biofragments must be able to sufficiently disperse so as to be useful in an affinity binding assay. This characteristic can be readily observed and/or established by routine methods. In some embodiments, the biofragments are derived from larger bioparticles that are insoluble or less soluble in equivalent solution conditions.

In some embodiments, the bioparticle fragment is isolated, purified, or removed from bioparticle fragments (and potentially other cellular or bioparticle debris) that do not contain a heterologous antigen-bonding molecule, and/or bioparticles that have not been disrupted or fragmented (e.g., whole-cell bioparticles). In some embodiments, the isolation, purification, or removal is merely partial, such that some debris remains. In some embodiments, the isolation, purification, or removal is substantial, such that the majority (e.g., 50% or more) of the debris, or fragments not containing a heterologous antigen-bonding molecule, are removed. In some embodiments, the bioparticle fragments with at least one heterologous antigen-bonding molecule can be removed from the other components of the solution or mixture by affinity purification based on a particular antigen or epitope tag contained in the heterologous antigen-bonding molecule. Illustrative, non-limiting examples of suitable epitope tags include c-myc, HA, FLAG-tag, GST, 6HIS, VSVg, V5, HSV, AU1, and others that are well known in the art. As will be recognized by persons of ordinary skill in the art, such epitope tags can be optionally multimerized to create repeating units of the epitope tag. As described below, the affinity-based isolation or purification process can be performed during the assembly of an antigen-detection assay system, where an immobilized epitope-tag binding molecule binds to the epitope tag present in the heterologous antigen-binding molecule. Other techniques to separate the biofragments containing at least one heterologous antigen-bonding molecule, from debris and/or biofragments that do not contain at least one heterologous antigen-bonding molecule include filtration, centrifugation, sedimentation, and other techniques known in the art.

As used herein, the term "heterologous antigen-binding molecule" is used to refer to any molecule that binds to an antigen. The term "heterologous" specifically refers to the characteristic that the antigen-binding molecule is not naturally occurring in or on the bioparticle (or biofragment thereof), but rather is caused to be expressed in and/or displayed on the bioparticle by experimental manipulation. In preferred embodiments, the heterologous antigen-binding molecule selectively binds to its cognate antigen (e.g., the antigen of interest) as compared to a non-cognate antigen. The term "selectively binds" is used to refer to the enhanced affinity and avidity binding characteristics of the heterologous antigen-binding molecule for the cognate antigen as compared to the non-cognate antigen. For example, in some embodiments, the heterologous antigen-binding molecule can bind to its cognate antigen with 5%, 10%, 25%, 50%, 75% or greater efficiency as compared to any non-cognate antigen. In preferred embodiments, the heterologous antigen-binding molecule can bind to its cognate antigen with an efficiency that is more than 2, 5, 10, 20 times or more as compared to binding to its non-cognate antigen.

In some embodiments, the heterologous antigen-binding molecule is an antibody-like molecule. As used herein, the term "antibody-like molecule" encompasses antibodies or fragments thereof, derived from any antibody-producing animal (e.g., fish, reptiles, birds, and mammals, including mice, rats, rabbits, camelids, and primates, including human). Unless otherwise stated, exemplary antibody-like molecule can include antibodies such as monoclonal, multispecific antibodies (e.g., bispecific antibodies), chimeric antibodies, anti-idiotype antibodies, and may be any intact molecule or fragment thereof, and of any isotype. Also, the antibody-like molecule encompasses molecules that comprise any of the foregoing, such as fusion proteins.

As used herein, the term "antibody fragment" refers to a portion derived from or related to a full-length antibody, generally including the antigen-binding or variable region thereof. Illustrative examples of antibody fragments include Fab, Fab', $F(ab)_2$, $F(ab')_2$ and Fv fragments, scFv fragments, diabodies, linear antibodies, single-chain antibody molecules and multispecific antibodies formed from antibody fragments.

As used herein, the term "single-chain antibody" refers to an antibody fragment that contains at least one antigen-binding region in a single polypeptide molecule. For example, as used herein, the term "single-chain Fv" or "scFv" specifically refers to an antibody fragment that comprises the $V_H$ and $V_L$ domains of an antibody, wherein these domains are present in a single polypeptide chain. Additionally, the Fv polypeptide further comprises a polypeptide linker between the $V_H$ and $V_L$ domains, which enables the scFv to form the desired structure for antigen binding. An scFv can also be generated to be multivalent, namely to contain multiple pairings of $V_H$ and $V_L$ domains in a single polypeptide chain, where each pairing can bind to the same or different antigen.

Other exemplary single-chain antibodies include single-chain Fab fragments (scFab) and nanobodies. The term single-chain Fab fragments (scFab) refers to an antibody fragment that comprises a single fragment antigen-binding region (Fab) of an antibody in a single polypeptide chain, typically with a peptide linker between the H and L chain fragments. The term "Nanobody®" refers to an antibody fragment that consists of a single polypeptide monomeric variable antibody domain that is able to specifically bind antigens. Nanobodies can include $V_HH$ fragments, which refers to fragments of heavy chain antibodies from camelids, and $V_{NAR}$ fragments, which refers to fragments of heavy-chain antibodies derived from cartilaginous fish.

In other embodiments, the heterologous antigen-binding molecule is a T-cell receptor. Like antibodies, T-cell receptors (TCR) are members of the immunoglobulin superfamily of proteins and function to recognize and/or bind to antigens. In vertebrate immune system, TCRs recognize antigens presented on the MHC. Native TCRs exist in αβ and γδ dimeric forms, which are structurally similar. When dimerized, the αβ and γδ forms appear very similar to an Fab fragment of a typical antibody. Accordingly, in the present embodiments, the heterologous antigen-binding molecule comprises antigen-binding portions of a TCR. As with antibodies, the antigen-binding portions of a TCR include engineered single-chain TCRs and TCR fragments comprising the variable regions of α, β, γ and δ chains, alone or paired in various combinations. Display of TCRs in single-chain and dimeric form on ribosomes, bacteriophage, cell, or proteinaceous particle is described in International Publication No. WO 2004/044004, incorporated herein by reference for this purpose and in its entirety.

In the fragmented state, the biofragment displays on its surface at least one heterologous antigen-binding molecule. As used herein, the term "display" refers to the position of the antigen-binding molecules in the surrounding aqueous environment immediately around the biofragment. The antigen-binding domains of the molecules are in communication with the surrounding environment and are, thus, capable of coming into physical contact with and binding their cognate antigens. However, as implied by the term "display," the antigen-binding molecules remain anchored or connected to the biofragment. In some embodiments, the heterologous antigen-binding protein is a fusion with a domain of a protein that is endogenous to the initial bioparticle and that spans the outer surface (e.g., plasma membrane, cell wall, capsid, and the like). Such domains are known in the art for various bioparticles. For example, as described above, the display of exogenous proteins on M13 filamentous bacteriophages can utilize fusions with coat proteins pIII, pVI, pVII, pVIII, and pIX. Additionally, as described below, libraries of yeast cells displaying human scFv utilized Aga1-Aga2 to tether the human scFv to the yeast cell walls. However, there is no requirement that the heterologous antigen-binding molecule be displayed on the exterior side of the bioparticle surface. Instead, in the original, non-fragmented bioparticle the at least one heterologous antigen binding molecule can be attached to or displayed on the internal or external side of the bioparticle surface. Upon fragmentation, even previously internal, surface-bound heterologous antigen binding molecules are accessible to the external environment due to the fragmentation of the bioparticle surface.

As used herein, the term "antigen of interest" refers to any antigen that serves as a cognate antigen to the heterologous antigen-binding molecule. It will be apparent to persons of ordinary skill in the art that there is no limitation on the character, type, or source of antigen in the practice of the present invention. For example, embodiments of antigens can include toxins, biomarkers for microbial or parasitic infection, biomarkers for the presence of transformed cells, such as cancer cells, biomarkers for a biological state, such as a disease state, and endogenous biomarkers indicating a particular genotype or phenotype. Antigens can be peptides, polypeptides, and non-protein antigens. In some embodiments, the antigens are non-protein small molecule compounds, such as drugs, metabolites, environmental pollutants, and the like.

In another aspect, the described biofragment compositions can be employed in methods for detecting and/or selectively binding an antigen of interest in a sample, such as a biological sample. In some embodiments, the biofragment compositions can be used as a capture reagent that selectively binds to the antigen of interest (i.e., molecules comprising the cognate antigen for the displayed heterologous antigen-binding protein) and does not bind the other non-cognate antigens present in the sample. Thus, any antigen of interest that is bound to the biofragment composition can be selectively removed from the other components of the sample. Detection of binding can be accomplished according to various assay formats known in the art. Illustrative examples are described in more detail below. In other embodiments, the described biofragment compositions can be used as part of a detection reagent that selectively binds to the antigen of interest (i.e., molecules comprising the cognate antigen for the displayed heterologous antigen-binding protein) that have been previously captured, and does not bind the other non-cognate antigens present in the captured sub-sample.

Accordingly, in one embodiment, the method comprises contacting a sample with a biofragment composition as described herein under conditions sufficient to permit the binding of the biofragment compositions (via the heterologous antigen-binding protein) to the antigen of interest, and detecting the binding of the biofragment compositions to the antigen of interest.

In some embodiments, the method comprises immobilizing the biofragment composition. As will be recognized in the art, the biofragment compositions can be immobilized via attachment directly or indirectly to an appropriate solid support. This can be performed through use of an immobilized epitope-binding molecule, such as described in more detail below. By virtue of immobilization, the biofragment compositions can serve as an antigen-specific capture reagent to facilitate detection, isolation, and/or purification of the antigen.

In some embodiments, the method further comprises contacting the sample with a detection reagent that also binds to the antigen of interest. While it is preferred that the detection reagent specifically binds to the antigen of interest, it is not critical that it demonstrates a high degree of specificity because the specificity is provided in the assay by the biofragment composition. However, it will be apparent that the detection reagent should not compete with the binding of the biofragment composition to the antigen of interest. Nonlimiting examples of the detection reagent include polyclonal antibodies (e.g., as included in a polyclonal antiserum), monoclonal antibodies, TCRs, lectin, and any known natural binding partner to the antigen.

In a further embodiment, the detection reagent is detectably labeled. Detectable labels can include, but are not limited to, functional enzymes, chemiluminescent molecules, fluorescent molecules, phosphorescent molecules, radioactive labels, spin labels, redox labels, and the like, specific examples of which are well known in the art.

In some embodiments, the detection reagent provides a detectable signal with the further participation of a reporter reagent, which is also provided in the method. The reporter reagent performs as a secondary detection reagent, wherein the reporter reagent binds to a component common to the (primary) detection reagents.

In preferred embodiments, the method contains a step wherein the biofragment/antigen/detection reagent complex is separated from any unbound detectable label. In a standard ELISA context, the complex is typically immobilized on a solid substrate, such as the bottom of a well. The unbound reagent with a detectable label is removed by one or more rinse procedures. In some methods of the present invention, no immobilization is required by virtue of the size of the biofragment, which facilitates the separation of the labeled biofragment/antigen complex from unbound detectably-labeled reagent and/or unbound antigen. In other methods, the biofragment can be immobilized to solid surfaces such as a biofragment plate or electrode. Simple wash protocols can be used. In some embodiments, centrifugation can be employed to generate pellets followed by resuspension in a wash buffer. This can be performed once or in a series to selectively isolate the labeled biofragment/antigen complex from unbound detectably label reagent and/or unbound antigen.

In some embodiments, the labeled biofragment/antigen complex is separated from unbound detection reagent, followed by detection and/or quantification by use of various assays known in the art. For example, an antibody sandwich flow cytometric assay (ASFC) can be used to quantify antigen binding by the biofragment. In another embodiment, the labeled biofragment/antigen complex is detected and/or quantified by use of an ELISA-like enzymatic assay, which does not necessarily require immobilization of the antigen/capture reagent complex. The labeled biofragment/antigen complex is quantified by use of a detection reagent bound to an enzyme with detectable activity, such as horseradish peroxidase (HRP). Upon separation of the labeled biofragment/antigen complex from unbound detection reagent, the activity of the enzyme is quantified by virtue of a characteristic of the product of enzyme activity, such as a color change, or light absorbance at a specific wavelength.

In yet another embodiment, binding of the biofragment composition to the antigen complex is detected and quantified without the use of a labeled reporter, but rather is detected and quantified using a competitive inhibition assay. In a representative example, the assay comprises further contacting the sample with a detectably-labeled antigen of interest, wherein binding of the biofragment to any unlabeled antigen of interest from the sample blocks binding of the biofragment to the detectably-labeled antigen of interest. By virtue of the competitive binding with the biofragment, binding of the antigen of interest results in a detectable reduction of labeled antigen of interest bound to the biofragment compared to a control sample not containing any antigen of interest. See, e.g., Gray, S. A., et al., *Biotechnol Bioeng* 105:973-981 (2010).

In yet another embodiment, a separate detection reagent is not required. Instead, the successful "capture" of a cognate antigen by the biofragment composition can be detected electrochemically. For example, in one embodiment, the binding of the biofragment composition to the cognate antigen can be detected with techniques such as by faradaic electrochemical impedance spectroscopy, which is described below in more detail. Briefly, in faradaic electrochemical impedance spectroscopy a conductive or semi-conductive substrate, such as an electrode, is used as a solid support. The biofragment composition is immobilized directly or indirectly to the conductive or semi-conductive surface of the substrate, through conventional methods. By using an electroactive molecule, the binding of the cognate antigen is detected by sensing the differences in electrical (or current) transfer resistance when an antigen binds to the biofragment composition, as compared to when the antigen is not present. The additional chemical bulk of the antigen, in combination with the heterologous antigen-binding agent and its connected bioparticle fragment, and potentially other tether constructs, contributes to a barrier to the interfacial electron transfer among the electroactive molecules, which is detected through the electrode via any commonly known device that can monitor electrical current, potential, or impedance.

The foregoing presentation of the method embodiments are generally in the context of the biofragment composition serving as a capture reagent, permitting subsequent detection (through affinity or electrochemical techniques). However, the invention is not limited to this aspect. Persons of ordinary skill in the art will recognize that alternative capture reagents can be used that incorporate antigen-specific binding molecules. Non-limiting examples include magnetic beads conjugated to polyclonal antibodies (antiserum), immobilized antibodies, antibody-like molecules, or fragments thereof, lectins, TCRs, or any naturally occurring binding partner. After capturing the cognate antigen from the sample, the biofragment compositions of the present invention can be used as part of a detection reagent. Detection/quantification of binding of the biofragment composition (or detection reagent comprising the biofragment) to the captured antigen can be performed by incorporating any well-known detectable label, or by use of a detectably-labeled secondary detection reagent specific for a component of the biofragment composition.

In some embodiments, the sample is a biological sample. Non-limiting examples of biological samples include blood, urine, sputum, mucus, saliva, cerebral spinal fluid, tissues, stool, or processed derivatives thereof. Use of such samples can facilitate the use of the methods of the present invention for purposes of detecting particular biological states, the presence of pathogens, parasites, or to determine particular phenotypes, depending on the antigen of interest. In additional embodiments, the sample is an environmental sample, such as a water sample. In additional embodiments, the sample is from a nutrient source, such as from the food or potable water supply, for example, milk, juice, meat, crop samples, animal feed, and the like, or any processed derivatives thereof The methods of the present invention can be applied to the monitoring of these samples to monitor for toxins and contaminants, or, for example, in efforts to monitor against agents used in acts of bioterrorism.

In another aspect, the disclosure provides a method of detecting the presence of an antigen of interest in a biological sample. The method comprises contacting a sample, such as a biological sample, to the biofragment composition described herein under conditions sufficient to permit the binding of the antigen of interest to the biofragment composition. The biofragment composition is immobilized, directly or indirectly, to a conductive or semi-conductive electrode surface. The method also comprises measuring the electron transfer resistance at the electrode surface in the presence of an electroactive molecule, wherein binding of the antigen of interest to the biofragment composition is detected by a change in the electron transfer resistance as compared to the electron transfer resistance when the antigen of interest is not present.

As used herein, the term "electroactive molecule" is any molecule that can participate in or facilitate the transfer of electrons (e.g., electrical current) in an aqueous solution. Such electroactive molecule can be any appropriate electrolyte, as known in the art of electrochemical impedance spectroscopy. For example, the electroactive molecule can be a redox probe, such as $[Fe(CN)_6]^{3-/4-}$, and the like.

The electrode surface can be any surface that is conductive or semi-conductive, such that it is appropriate for detection of electrical potential, current, or impedance. An example is a gold-surface electrode, including Gold (AU) marcrodisk working electrodes or screen-printed gold electrodes, each of which are described in more detail below.

In some embodiments, the biofragment composition is immobilized directly to the conductive or semi-conductive electrode surface. There are numerous known and commonly used methods to immobilize affinity agents, such as the biofragment compositions described herein, to electrode surfaces. For example, the biofragment composition can be immobilized to the conductive or semi-conductive electrode surface through known methods, including chemisorbant or physiosorbant crosslinking.

In some embodiments, the biofragment composition is immobilized indirectly to the conductive or semi-conductive electrode surface via one or more intervening tether constructs. The term "intervening tether constructs" can include a layer that directly anchors the complex to the electrode surface. The anchor layer can be a protein, such as BSA, an organic molecule, or an inorganic molecule. The anchoring construct can be attached directly to the electrode surface by, for example, chemisorbant or physiosorbant crosslinking. The biofragment composition can be linked to the anchoring construct directly, using known approaches, such as the appropriate use of biotin/streptavidin interaction, click chemistry, or epitope binding reagent binding to an affinity tag in the biofragment composition. In some embodiments, there are additional intervening tether constructs, which link the biofragment composition to the anchoring construct (and thus the electrode surface). For example, as described below, a biotinylated BSA layer on the electrode is linked to a multivalent streptavidin molecule. The streptavidin molecule is linked to a biotinylated epitope tag-binding antibody, which specifically binds to an epitope tag (e.g., HA) incorporated into the scFv of the biofragment composition. See also FIG. 1A.

Accordingly, in some embodiments, the present method includes the step of immobilizing the biofragment composition to the electrode surface (directly or indirectly with tether constructs). In some embodiments, the immobilizing step comprises attaching an anchor construct to the electrode, immobilizing an affinity-tag binding molecule to the anchor construct, and contacting the affinity-tag binding molecule with the biofragment composition. In these embodiments, the heterologous antigen-binding molecule of the biofragment composition comprises an affinity tag, such as described above. As described below, the scFv component of the biofragment included an HA epitope tag, which was bound by an anti-HA antibody, which in turn was linked via biotin/streptavidin interactions with the BSA anchor on the electrode.

In some embodiments, this immobilizing step serves to isolate, purify, or remove the biofragment compositions with the at least one heterologous antigen-binding molecule from fragments of the bioparticle that do not have at least one heterologous antigen-binding molecule (and/or other debris or unfragmented bioparticles). Accordingly, some embodiments of the method include rinsing steps after any of the assembly steps addressing the anchor, additional intermediate tether components, and/or the biofragment composition.

In another aspect, the disclosure provides a method for making the biofragment composition. The method can include the initial step of generating a bioparticle that contains a heterologous antigen-binding molecule. As described above, this can be accomplished by causing the expression of the heterologous molecule in a cell or other particle of interest. The expressed heterologous protein is caused to attach to, or assemble upon the outer surface (either internally or externally on the surface) of the bioparticle. The bioparticle is then fragmented according to any appropriate techniques, such as mechanical disruption of the particle surface using a mortar and pestle. In some embodiments, the biofragments are isolated or purified from the other components of the solution resulting from the mechanical disruption.

The disclosed method can be incorporated into methods of detecting the antigen. For example, in one embodiment, the step of immobilizing the biofragment compound to the electrode surface (or other solid support) can coincide with the step of isolating, removing, or purifying the biofragments with at least one heterologous antigen-binding molecule in part, substantially, or completely, from other biofragments in the mixture. Thus, the immobilizing step described above can comprise additional steps, such as contacting the affinity-tag binding molecule with the plurality of bioparticle fragments to the affinity-tag binding molecule, and removing the bioparticle surface fragments that remain unbound to the immobilized affinity-tag binding molecule. Furthermore, the immobilizing step described above can also comprise (or be preceded by) the initial step of disrupting the surface of one or more bioparticles that have at least one attached heterologous antigen-binding molecule attached thereto to produce a plurality of bioparticle surface fragments.

In another aspect, the present disclosure provides an antigen detection system. The system comprises the biofragment composition described herein. The biofragment composition is immobilized directly or indirectly to a conductive or semi-conductive electrode surface, as described herein. The system also comprises an electroactive molecule, as described herein, and a device to monitor electric current, electric potential, and/or electric impedance. Such devices are regularly used and commonly available. Illustrative devices useful for implementation in the system include a potentiostat and a galvanostat. Such devices can be battery operated, thus facilitating the implementation of the system into simple and convenient point of care devices and set-ups that can be operated in the field where consistent access to electricity may not be available. The electrode surface can be any conductive or semi-conductive electrode, for example, a screen-printed gold electrode, as described herein.

In another aspect, the present disclosure provides a device for detecting an antigen of interest, wherein the device implements the system and biofragment probes described herein.

In another aspect, the present disclosure provides methods for validating a candidate antigen as a biomarker for a biological state, as described in WO 2012/159075, incorporated herein by reference. Briefly, an antigen of interest can be contacted to a library of bioparticles or biofragments derived from bioparticles with heterologous antigen-binding molecules. In other embodiments, the library can be contacted with one or more antigens obtained from target and control samples (such as disease state and healthy state). The binding of the antigen or antigens is determined, and the bioparticles that bind to the candidate biomarker antigens (or the bioparticles from which the binding biofragments were derived) are propagated to produce a clonal or near clonal population of bioparticles that can serve as a source of biofragments affinity reagents. The bioparticles or biofragments thereof can be stored, such as through lyophilization, as described in WO 2012/159075, incorporated herein by reference.

The following is a description of the initial development of a cell-free affinity reagent comprising a yeast-scFv biofragment probe that can selectively bind an antigen of interest. Furthermore, the description provides a representative method for using the affinity reagent in an electrochemical detection assay that incorporates a gold electrode and does not require labels or an additional set of antigen-specific detection or capture reagents. This is also described in Grewal, Y. S., et al., "Label-free electrochemical detection of an *Entamoeba histolytica* antigen using cell-free yeast-scFv probes," *Chem. Commun.* 49:1551-1553 (2013), hereby expressly incorporated by reference in its entirety.

Abstract: Inexpensive, simple and quick detection of pathogen antigens in human samples is a key global health objective. Limiting factors include the cost and complexity of diagnostic tests that utilize antibody probes. Herein, we present a method for label-free electrochemical detection of a protein from the enteric pathogen *Entamoeba histolytica* using cell-free yeast-embedded antibody-like fragments (yeast-scFv) as novel affinity reagents.

Description: The waterborne pathogen *E. histolytica* is a prevalent but treatable disease that is estimated to cause 100,000 deaths annually in developing countries. Prior detection techniques relied on microscopy and serology. Microscopy tests cannot distinguish between *E. histolytica* and closely related non-pathogenic commensals that also occur in stool, most notably *E. dispar*. Serological tests, which detect serum antibodies against *E. histolytica*, cannot distinguish between past and current infection. For these reasons molecular tests, such as ELISA, have become preferred diagnostics to identify *E. histolytica* infection, due to their specificity and sensitivity.

ELISA-based methods have the limitation of being reliant on highly specific affinity reagents, typically monoclonal antibodies (mAbs). The considerable time and resources required for the generation of mAbs is a bottleneck in biomedical research and the development of new diagnostic tests. Potential alternatives to mAbs are fragments of antibodies known as single-chain variable fragments (scFv). In contrast to traditional mAbs derived from vertebrate animals, scFv reagents can be cheaply and rapidly selected from yeast-display and other libraries. In yeast display, libraries of genetically engineered *Saccharomyces cerevisiae* cells display on their surfaces diverse scFv molecules derived from human mRNA. By using fluorescence-activated cell sorting (FACS), it is possible in a 2-3 week process to screen yeast display libraries for clones that bind specifically to antigens. If needed, affinity enhancement can be completed in another 3-4 weeks. Biosensors incorporating scFvs for specific antigen detection have been described.

Although many useful scFvs have been reported, most scFvs derived from display libraries perform unsatisfactorily in solution. Like natural antibodies, antibody-like fragments culled from display libraries are products of selection. Yeast-displayed scFv are selected by FACS for affinity and stability when bound via Aga1-Aga2 linkages to yeast cell walls. Unfortunately, scFv that have excellent activity on yeast surfaces usually lose their activity in solution, an environment for which they were not selected. This problem has limited the penetration of scFv into diagnostic practice.

Affinity reagents composed of lyophilized whole yeast cells with displayed scFv (yeast-scFv) have been shown to be viable, cheap and quick alternatives to generating mAbs or soluble scFv for use in immunoassays. Yeast-scFv are robust and renewable reagents that can be produced in vast quantities at low cost. However these whole-cell reagents are insoluble and too large for many diagnostic applications. Moreover, they required the use of labeled polyclonal antibodies to detect antigen binding to the yeast-scFv particles. Although it was not necessary that the detection antibodies be highly specific to the antigen (monoclonal specificity was conferred by the yeast-scFv reagent), the requirement for a traditional animal-derived detection antibody diluted the benefits of using yeast-scFv.

To enable the use of yeast-scFv affinity reagents as full and practical alternatives to traditional antibodies, the current report describes two new approaches. First, cell-free yeast-scFv reagents, also referred to herein as "yeast-scFv biofragments", were generated by mechanical fragmentation of whole yeast-scFv cells, followed by combined mechanical and affinity-based purification of semi-soluble cell wall fragments bearing displayed scFv. Second an electrochemical (EC) approach was used to detect antigen binding to cell-free yeast-scFv, without the need for animal-derived detection antibodies. These approaches were combined to generate a specific, sensitive sensor for a candidate *E. histolytica* cyst protein.

The principle of faradaic electrochemical impedance spectroscopy (F-EIS) was used for label-free EC detection. This is one of the most effective methods for the label-free detection of biomolecules and for probing the build-up of the biomaterials sensing film on the electrodes. In F-EIS, the successful capture and detection of the biomolecule of interest, here an *E. histolytica* protein, is observed as a change in the capacitance and interfacial electron transfer resistance of a conductive or semiconductive electrode modified with the scFv capture probe. A typical shape for a F-EIS spectrum at a disk macroelectrode, presented in the form of a Nyquist plot (e.g., Z' versus Z" at variable frequencies, where Z' and Z" are the real and imaginary components), includes a semicircle region lying on the Z' axis followed by a straight line The semicircle portion, is observed at higher frequencies and corresponds to the electron-transfer-limited process. See, e.g., E. Katz and I. Willner, *Electroanalysis,* 15: 913-947 (2003) and A. J. Bard and L. R. Faulkner, *Electrochemical Methods: Fundamentals and Applications*, John Wiley & Sons, 2000. The diameter of the semicircle corresponds to the charge-transfer resistance at the electrode surface, $R_{ct}$ (also referred to in the art as the electron transfer resistance, or $R_{ct}$). Therefore, the build-up of an immunosensing layer and scFv-antigen complex formation can be followed by F-EIS, where the change in impedance of the electrode surface and its interface to the electrolyte solution containing a redox probe (e.g., $[Fe(CN)_6]^{3-/4-}$) at different stages of the immunosensor fabrication is measured in the form of its $R_{ct}$.

Figure 2:
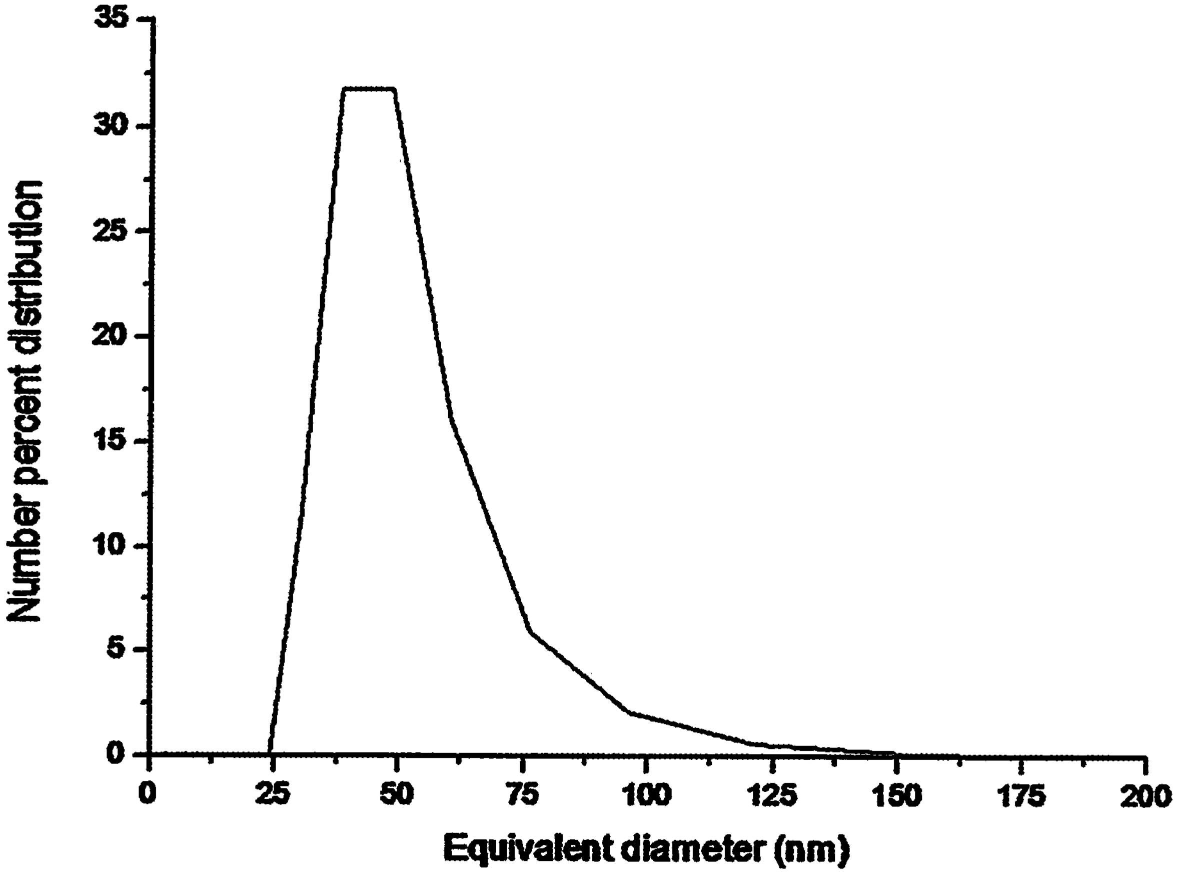
FIG. 2 graphically illustrates the dynamic light scattering (DLS) of yeast-scFv biofragments after application filtration through a 100 nm filter. Analysis performed on Malvern Zetasizer 3000 HSa using multimodal algorithm.

FIG. 1A outlines this approach for using a cell-free yeast-scFv biofragment reagent in the label-free detection of an *E. histolytica* antigen. Briefly, a biolayer on a gold (Au) surface is formed with biotinylated BSA (bio-BSA). Multivalent streptavidin is used to link the bio-BSA to a biotinylated anti-human influenza hemagglutinin tag antibody (bio anti-HA). This complex is used to capture cell-free yeast-scFv biofragments by virtue of an HA antigen tag cloned into the recombinant scFv construct. The bound yeast-scFv fragment is then used to capture the target *E. histolytica* antigen (in this study, specifically protein EHI 115350, called '350' herein). To assure that the fragments were small enough to be useable in the bioassay, dynamic light scattering (DLS) measurements of the yeast-scFv fragments after filtration through a 0.1 μm filter was performed. The DLS data confirmed that fragments existed in the sub-100 nm size range (see FIG. 2), allowing for attachment of yeast-scFv fragments to bio anti-HA.

Figure 1B:
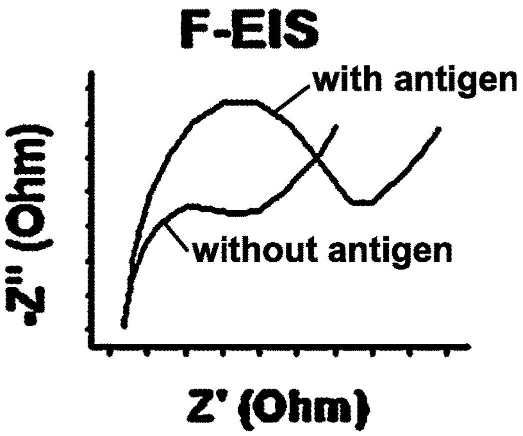
FIG. 1B and FIG. 1C are graphical representations of hypothetical sensor responses representing the presence and absence of *E. histolytica* proteins during the label-free impedance and voltammetric measurements, respectively.
Figure 1C:
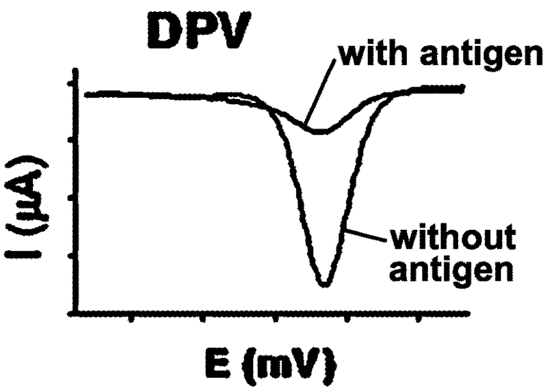
Figure 3A:
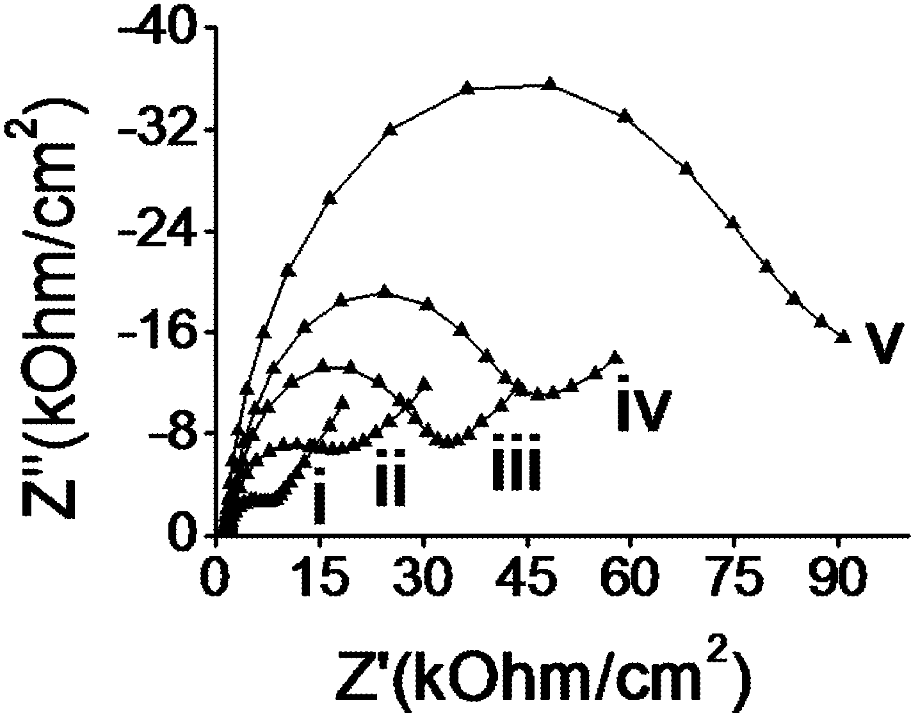
FIG. 3A illustrates Nyquist plots for (i) bare and sensing surfaces on gold electrodes, (ii) bio-BSA/streptavidin, (iii) bio-BSA/streptavidin/bio-anti-HA, (iv) bio-BSA/streptavidin/bio-anti-HA/yeast-scFv, and (v) bi-BSA/streptavidin/bio anti-HA/yeast-scFv/'350' antigen, each in 10 mM phosphate buffer solution (pH 7.4) containing 2.5 mM $K_3[Fe(CN)_6]$, 2.5 mM $K_2[Fe(CN)_6]$, and 0.1 M KCl.

The attachment of the bio-BSA, streptavidin, yeast-scFv biofragment, and *E. histolytica* antigens on the gold electrode was followed by the F-EIS and differential pulse voltammetry (DPV) (see, e.g., representative plots in FIGS. 1A and 1B). The BSA layer, in combination with subsequent attachment of streptavidin and antibody, act as a barrier for the interfacial electron transfer reaction of the $[Fe(CN)_6]^{3-/4-}$ process, resulting in an increase in $R_{ct}$. When we monitored $R_{ct}$ generated by the $[Fe(CN)_6]^{3-/4-}$ process before and after protein binding, there was a clear correlation between the presence of the target *E. histolytica* antigen and the increases of the $R_{ct}$ (FIG. 3). The presence of the *E. histolytica* antigen appears to further block the $[Fe(CN)_6]^{3-/4-}$ process from accessing the electrode surface effectively. The bare gold electrode (i) gave rise to the lowest semicircle domain indicating the fastest electron transfer (e.g., the lowest $R_{ct}$) followed by the bio-BSA/streptavidin-coated gold electrode (ii), bio-anti-HA (iii), yeast-scFv antibody immobilized electrode (iv), and target antigen (100 pg/mL) (v). These results indicate the successful stepwise binding of the biomolecules on the sensor surface.

Figure 3B:
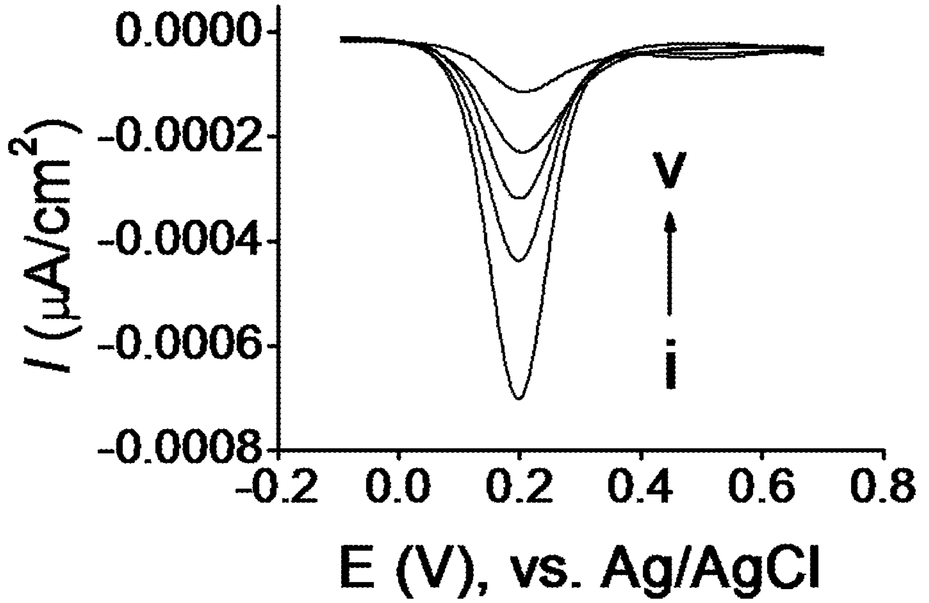
FIG. 3B graphically illustrates the differential pulse voltammetry (DVP) responses corresponding to complexes (i)-(v), as described above for FIG. 3A.

The risk of false-positive responses for targets at low concentrations is well-known when using a detection technique based on attenuation of the interfacial electron transfer reaction of a redox process. To assess the risk of achieving false-positive responses in F-EIS, a series of parallel independent DPV measurements were conducted. FIG. 3B shows the differential pulse profiles, where the peak current decreases in response to increasing the hindrance of the interfacial electron transfer reaction of the $[Fe(CN)_6]^{3-/4-}$ process. This is in line with the results observed in Faradaic EIS by the same electrode.

The specificity of the immunosensor towards '350' antigen was examined by attempting to capture an antigen that was nonspecific to the immobilized yeast-scFv probes. The Jacob protein of *E. histolytica* was previously shown not to bind with 350-specific yeast-scFv. Non-specific binding of the Jacob protein to the cell-free yeast-scFv probes was evaluated by using F-EIS and DPV measurements. A relatively high concentration of the Jacob protein (500 pg/mL) was used to maximize detection of background binding. A slight increase in the impedance (e.g., $R_{ct}$ value) and decrease in the DPV peak current (FIGS. 4A (i) and 4B (i)) were seen for the bio-BSA/streptavidin/bio-anti-HA/yeast-scFv/Jacob-coated electrode compared to that of the bio-BSA/streptavidin/bio-anti-HA/yeast-scFv-coated electrode (dotted line in FIG. 4A). A likely explanation for this observation was that the traditional BSA blocking method used in this approach could allow some degree of non-specific adsorption of the Jacob antigen. However, the signal changes for 500 pg/mL Jacob antigen were smaller than that produced by the target '350' antigen even when the latter was present at 50-fold lower concentration (10 pg/mL). This indicates that label-free immunosensing with a cell-free yeast-scFv reagent has specificity toward the target antigen.

Figure 4A:
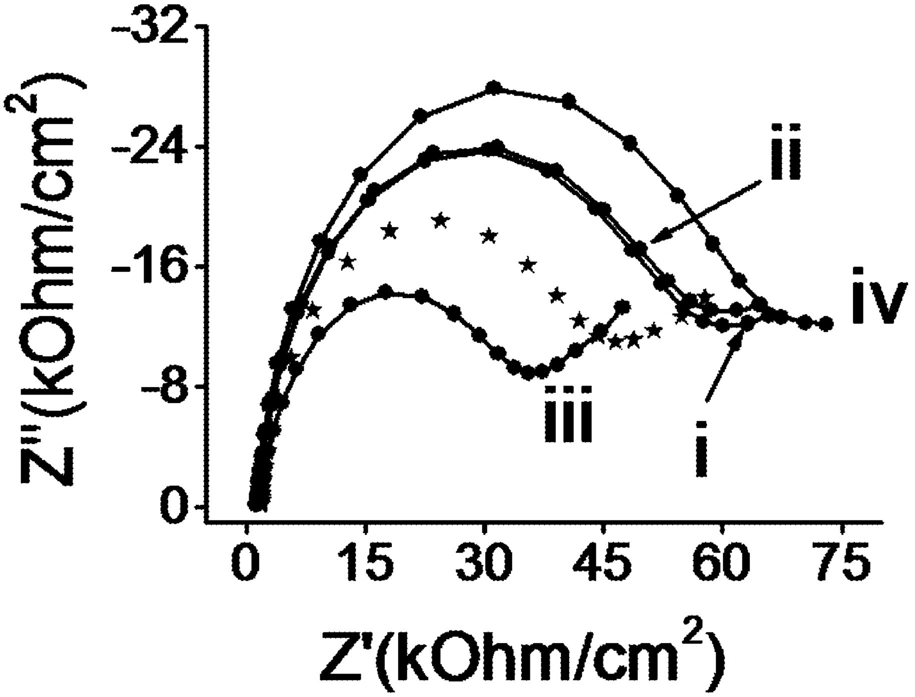
FIG. 4A illustrates Nyquist plots for immunosensing layer on gold electrodes for detecting (i) bio-BSA/streptavidin/bio-anti-HA/yeast-scFv/Jacob, (ii) bio-BSA/streptavidin/bio-anti-HA/yeast-scFv biofragment—2/'350', (iii) bio-BSA/streptavidin/bio-anti-HA/'350', and (iv) bio-BSA/streptavidin/bio-anti-HA/yeast-scFv biofragment/'350' immunocomplex formation, each in 10 mM phosphate buffer solution (pH 7.4) containing 2.5 mM $K_3[Fe(CN)_6]$, 2.5 mM $K_2[Fe(CN)_6]$, and 0.1 M KCl. Target protein concentrations for (i), (ii), (iii) and (iv) were 500, 500, 500, and 10 pg/mL, respectively. Dotted line spectrum represents impedance at bio-BSA/streptavidin/bio-anti-HA/yeast-scFv sensing layer in the same electrolyte solution. (B) Corresponding DPV current responses.

To further assess whether the yeast cell wall fragment may contribute to non-specific adsorption of antigens, a second yeast scFv fragment that is specific to an orthogonal *E. histolytica* antigen (named '780') (hereafter referred to as yeast-scFv-2) was used as a control. FIGS. 4A (ii) and 4B (ii) show the impedance and DPV responses obtained for 500 pg/mL '350' antigen at yeast-scFv-2 coated electrode. Compared to the response for 10 pg/mL '350' antigen at cognate yeast-scFv coated sensing layer (FIGS. 4A (iv) and 4B (iv), the use of yeast-scFv-2 significantly decreased the sensor impedance (e.g., lower $R_{ct}$) and increased the DPV peak current, even when a 50-fold higher concentration of '350' antigen was used. Thus, the non-cognate yeast-scFv-2 reagent failed to capture '350' antigen with the same efficiency as the cognate yeast-scFv reagent. It was also noted that a similar $R_{ct}$ and peak current values to Jacob antigen were observed, which might indicate a low level of nonspecific adsorption of antigen on yeast cell wall.

Figure 4B:
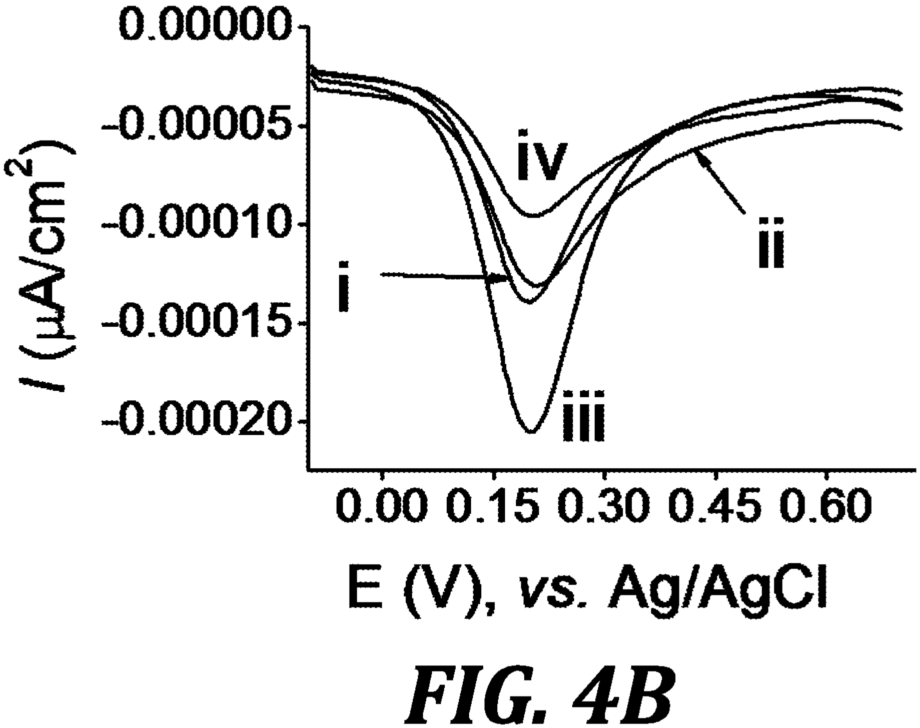
FIG. 4B graphically illustrates the differential pulse voltammetry (DVP) responses corresponding to complexes (i)-(v), as described above for FIG. 4A.

To assess the background noise, an assay was performed which excluded the yeast-scFv layer (FIGS. 4A (iii) and 4B (iii)). This assay detected non-specific interaction and adsorption of the '350' antigen on the bio BSA/streptavidin/bio anti-HA electrode. The $R_{ct}$ and DPV peak currents without yeast-scFv are comparable to the $R_{ct}$ and peak currents to the bio anti-HA surface (see FIG. 3 (iii) versus FIG. 4 (iii)). These results demonstrate that detection of '350' antigen by the label-free assay is a function of specific interactions between the cell-free yeast-scFv reagent and the antigen, and not to non-specific interactions between the antigen and other components of the assay.

Figure 5:
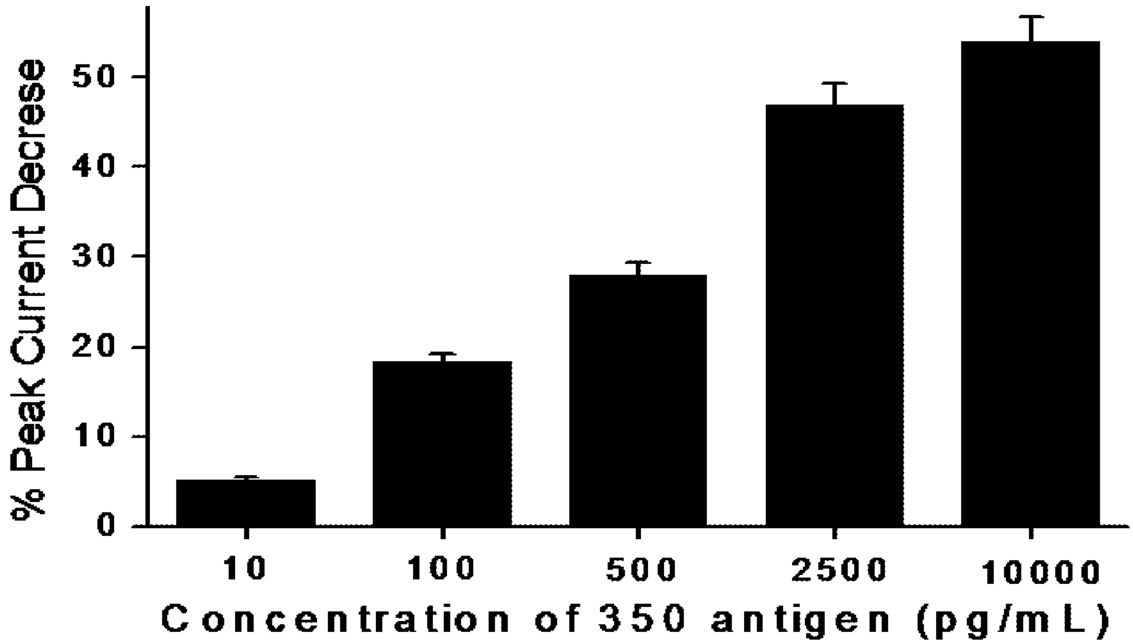
FIG. 5 graphically illustrates the change of the DPV peak currents at the immunosensing surface after incubation with designated concentrations of target *E. histolytica* '350' antigen.

To assess the dynamic range for detection of '350' antigen, the percent changes in DPV current responses (see below Example for illustrative calculation details) were measured before and after incubation of the yeast-scFv-modified electrode with designated concentration of '350' antigens (10 pg/mL to 10 ng/mL). Signals increased quantitatively with antigen concentration (FIG. 5). Saturation of the Au surface begins to occur at 2500 pg/mL (3.5 μM) of 350 antigen. Detection of the antigen above background was confirmed down to 100 pg/mL (558 pM). This concentration of antigen was similar to the limit of detection of the same antigen by a whole yeast-scFv probe used in combination with fluorescently labeled polyclonal signal antibody, as described previously. A precise lower limit of detection was not determined in this experiment.

Conclusion: It is demonstrated herein that a label- and cell-free electrochemical immunoassay towards an *E. histolytica* antigen using antibody fragments embedded in yeast cell wall fragments function as capture probes. The principle of this cell-free yeast-scFv based assay is not limited to *E. histolytica* 350 antigen, because the immunosensor could be fabricated towards any protein-based disease marker by selecting new yeast-scFv biofragments against any such antigen. Moreover due to the high sensitivity, technological simplicity, and quantitative output of label-free detection using yeast-scFv capture probes, as compared to flow cytometer based assay, this immunoassay has excellent potential to translate into a diagnostic application.

The following is a description of a subsequent, expanded study including the generation of additional cell-free affinity reagents comprising yeast-scFv biofragments that can selectively bind other antigens of interest. Furthermore, the described yeast-scFv biofragments were applied in an electrochemical detection assay that, as above, does not require labels or an additional set of detection reagents. However, the electrochemical detection assay described below incorporates the use of disposable (screen-printed) electrodes that have the advantage of very low cost. Finally, the study described below establishes that the yeast-scFv biofragments can specifically bind and allow detection of *E. histolytica* antigen in human stool samples, demonstrating the utility of the reagents and detection method in point of care situations.

Abstract: The time and costs associated with monoclonal antibody production limit the potential for portable diagnostic devices to penetrate the market. Replacing the antibody with a low-cost alternate affinity reagent would reduce the costs of diagnostic development and use, and lead to new portable diagnostic devices towards many diseases. Herein, low-cost affinity reagents, yeast-scFv biofragments, are described. These biofragment affinity reagents can be integrated into more traditional detection assay system, or used in a novel, label-free electrochemical based detection of antigens. As demonstrated herein, the label-free electrochemical-based detection can incorporate commercially available, inexpensive, and portable screen-printed electrodes to detect antigens of interest, such as *E. histolytica* cyst antigens. As described, the biosensor was able to detect antigen at concentrations of antigen down to 10 pg/mL in buffer with an inter-assay reproducibility of (% RSD, n=3) 4.1%. The ability of two differently engineered yeast-scFv biofragments to each specifically detect their cognate *E. histolytica* cyst antigens was demonstrated in a biological matrix derived from human stool. Because of the simple, inexpensive, and sensitive nature of this methodology, it provides a sensitive and low-cost alternative to immunosensors based on antibody-target recognition.

Introduction: Developing countries and remote areas require diagnostics that are portable, low-cost, quick, and easy to use, to ensure patients are expeditiously and accurately treated to control the spread of infectious disease. In these regions, laboratory tests are often not viable for reasons of cost and logistics. Screen-printed electrodes are inexpensive single-use electrodes that are produced by printing various inks, such as gold and carbon, on different types of plastics or ceramics. Due to their relative low cost compared to traditional electrode materials, screen-printed electrodes can be suitable components in future point-of-care devices. Electrochemical biosensors utilizing screen-printing technology have found commercial success for diabetes management, and have been demonstrated for the detection of various waterborne pathogens.

*Entamoeba histolytica* (*E. histolytica*) is waterborne pathogen which causes up to 100,000 deaths annually in developing countries, and as such, it has been the focus of diagnostic development to accurately detect *E. histolytica* infection at point of care. Microscopy and serology are common diagnostic techniques, however, these are (respectively) inadequate in accurately identifying *E. histolytica* from closely related non-pathogenic commensals in stool and discriminating from past and current infection. Additionally, PCR tests towards *E. histolytica* are increasingly common, but they are too expensive for most settings where *E. histolytica* disease is endemic. New specific and sensitive detection tests are required to overcome these limitations. Molecular tests, such as enzyme-linked immunosorbent assay (ELISA), are able to fulfill these criteria, and are now favored tests to identify *E. histolytica* infection.

However, ELISA-based methods are limited by their dependence on highly specific affinity reagents, typically monoclonal antibodies (mAbs). The generation of mAbs necessitates considerable costs in time and resources. This has constrained advancements in biomedical research and diagnostic development. Single-chain variable fragments (scFv) are affinity reagents which have the potential to overcome the limitations imposed by mAbs. Unlike traditional vertebrae animal-derived mAbs, scFv reagents can be inexpensively and quickly selected from a yeast- (or phage-) display library.

There are numerous demonstrations of biosensors incorporating scFv affinity reagents, however, many scFvs derived from display libraries perform unsatisfactorily in solution. ScFv reagents culled from a display library are productions of selection. Unfortunately, selected scFv fragments, which have excellent activity on yeast surfaces, often lose their activity once in solution, an environment for which they were not selected. This decrease in activity has hindered adaption of scFv into diagnostic practice. To address this limitation, lyophilized whole yeast cells with displayed scFv (yeast-scFv) have been shown to function directly as affinity reagents and have been developed as low-cost, renewable alternatives to mAbs. Yeast-scFv can be quickly produced in vast quantities at a much lower cost than mAbs. However, yeast-scFvs are insoluble and too large for the adaption into many diagnostic applications. Yeast-scFv also require labeled secondary polyclonal antibodies to detect antigen binding to the yeast-scFv particles, hence complicating assay development and performance.

To address yeast-scFv limitations, cell-free yeast-scFv biofragment affinity reagents were developed by mechanical fragmentation of yeast-scFv cells. Cell wall fragments bearing displayed scFv were enriched by binding to surface-attached antibodies specific to the scFv's epitope tags. These reagents, also referred to herein as yeast-scFv biofragments, were developed as a replacement for monoclonal antibodies. See Grewal, Y. S., et al., *Chem. Commun.* 49:1551-1553 (2013), and the above description. This concept demonstrated the ability of the yeast-scFv biofragments to detect antibody/antigen capture combinations in a defined buffer medium, using laboratory-dependent gold disc macroelectrodes.

Faradaic electrochemical impedance spectroscopy (F-EIS) is a highly effective method for the label-free detection of biomolecules. Successful capture and detection of the biomolecule of interest using a yeast-scFv biofragment capture probe causes an observable change in the capacitance and interfacial electron transfer resistance of a conductive electrode. An F-EIS spectrum on an electrode (e.g., screen-printed electrode) is commonly presented in the form of a Nyquist plot with Z' versus Z" at variable frequencies, and where Z' and Z" are the real and imaginary components. At higher frequencies, the semicircle portion of the Nyquist plot is observed, which corresponds to the electron-transfer-limited process. The semicircle diameter is directly related to the electron-transfer resistance at the electrode surface, $R_{ct}$. Consequently, stepwise construction of the immunosensing layer and capture of antigen by the yeast-scFv biofragment complex can be observed by F-EIS, where the impedance change of the interface between the electrode surface and electrolyte solution, containing a redox probe (e.g., $[Fe(CN)_6]^{3-/4-}$), is measured in the form of its $R_{ct}$.

To develop and demonstrate yeast-scFv biofragments as alternative affinity reagents in diagnostics, these inexpensive affinity reagents were combined with commercially available disposable screen-printed gold electrodes, in place of the more expensive gold disk electrodes used for the initial proof of concept (described above and in Grewal et al., 2013). The system was validated by its use to detect recombinant *E. histolytica* antigens spiked into a complex biological matrix derived from human stool. Furthermore, a second set of yeast-scFv biofragments detecting an alternative *E. histolytica* antigen was examined with this system. This new combination indicates that yeast-scFv biofragments, like mAbs, can routinely be engineered to specifically capture any antigen of interest. The combination of yeast-scFv biofragments, the screen-printed electrode platform, and the ease of label-free electrochemical detection allows for simple, quick, and cheap analysis of antigens, such as antigens from such pathogens as *E. histolytica*.

Results and Discussion: FIG. 1A outlines the approach for the label-free detection of *E. histolytica* antigens using yeast-scFv biofragment affinity reagents on electrodes (e.g., screen-printed electrodes). Briefly, the gold electrode (AU) is coated with a biolayer of biotinylated BSA (Bio-BSA). Streptavidin is then used to link the bio-BSA to a biotinylated anti-human influenza hemagglutinin tag antibody (Bio anti-HA). A yeast-scFv biofragment (prepared from yeast-scFv clone '350-E2' or '030-L') is then captured by the use of a HA antigen tag cloned into the recombinant scFv construct. The bound yeast-scFv biofragment is then used to capture the target *E. histolytica* antigens (E. his antigen, e.g., '350' or '030). The utilized yeast-display library was constructed with the scFv already fused to HA and c-myc tags. Thus, beyond the 2-4 weeks required to isolate the yeast-scFvs, only a single, commercially available ("off-the-shelf") biotinylated anti-HA mAb was required to build the assay. This approach is far more cost effective than making monoclonal detection antibodies for every different antigen of interest.

Figure 6:
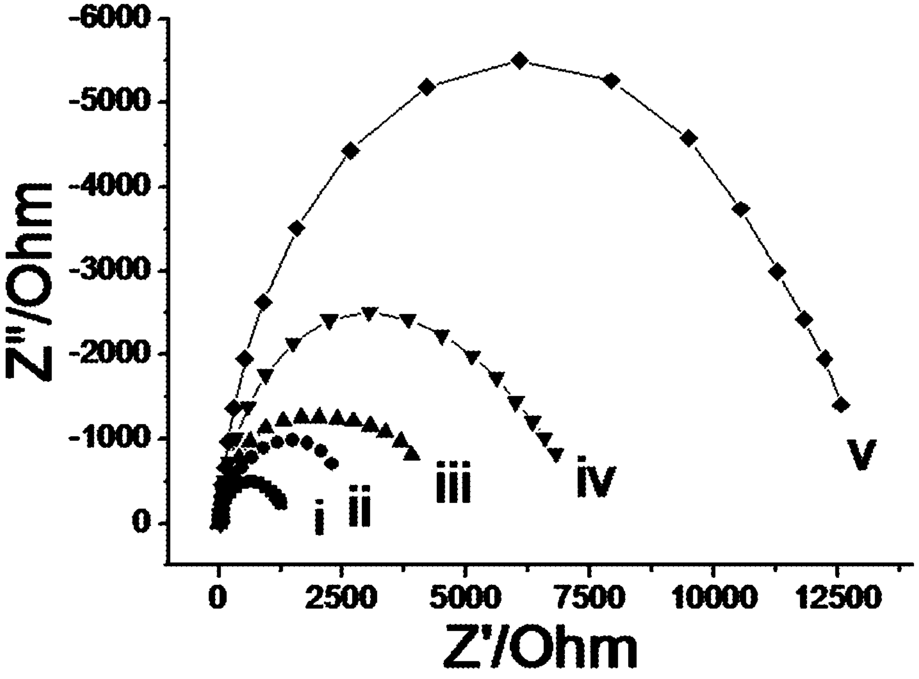
FIG. 6 is a Nyquist plot for (i) bio-BSA, (ii) bio-BSA/streptavidin, (iii) bio-BSA/streptavidin/bio-anti-HA, (iv) bio-BSA/streptavidin/bio-anti-HA/yeast-scFv biofragment, and (v) bio-BSA/streptavidin/bio-anti-HA/yeast-scFv biofragment/'350' immunocomplex, each determined using F-EIS-based assay with a gold coated screen-printed electrode and in 10 mM phosphate buffer solution (pH 7.4) containing 2.5 mM $K_3[Fe(CN)_6]$, 2.5 mM $K_2[Fe(CN)_6]$, and 0.1 M KCl.

The attachment of the bio-BSA, streptavidin, bio-anti-HA, yeast-scFv biofragments and *E. histolytica* antigens on the gold coated screen-printed electrode was measured by F-EIS (FIG. 6). The assay complex blocks the interfacial electron transfer reaction of $[Fe(CN)_6]^{3-/4-}$, subsequently increasing the $R_{ct}$. An increase in $R_{ct}$ is observed from the successive blocking of the electrode surface with the stepwise attachment of the streptavidin, the bio-anti-HA, and the yeast-scFv biofragment onto the bio-BSA modified screen-printed electrode (FIG. 6). Furthermore, there was a clear and drastic increase of the $R_{ct}$ generated from the $[Fe(CN)_6]^{3-/4-}$ process in the presence of *E. histolytica* antigen (FIG. 6, curve (v)). The bio-BSA modified screen-printed electrode (FIG. 6 (i)) gave rise to the lowest semicircle domain, followed by bio-BSA modified/streptavidin (FIG. 6 (ii)), bio-anti-HA (FIG. 6 (iii)), yeast-scFv biofragment (FIG. 6 (iv)), and target antigen (500 pg/mL) (FIG. 6 (v)). These results indicate successful stepwise construction of the biosensor. The biosensor was also highly reproducible with less than 5% relative standard deviation (RSD) between the inter-assay signals, at each step of the assay: (i) 1.2%, (ii) 2.13%, (iii) 4.76%, (iv) 3.00%, (v) 4.01%, n=3. To validate the assay construction as well as to assess the risk of possible false positive impedimetric responses in this assay, a series of control DPV measurements were conducted (data not shown) using biomolecule functionalized electrodes. The peak current decreases in response to an increase in the hindrance (i.e., via successive biomolecules attachment) of the electron transfer reaction of $[Fe(CN)_6]^{3-/4-}$ process.

Figure 7:
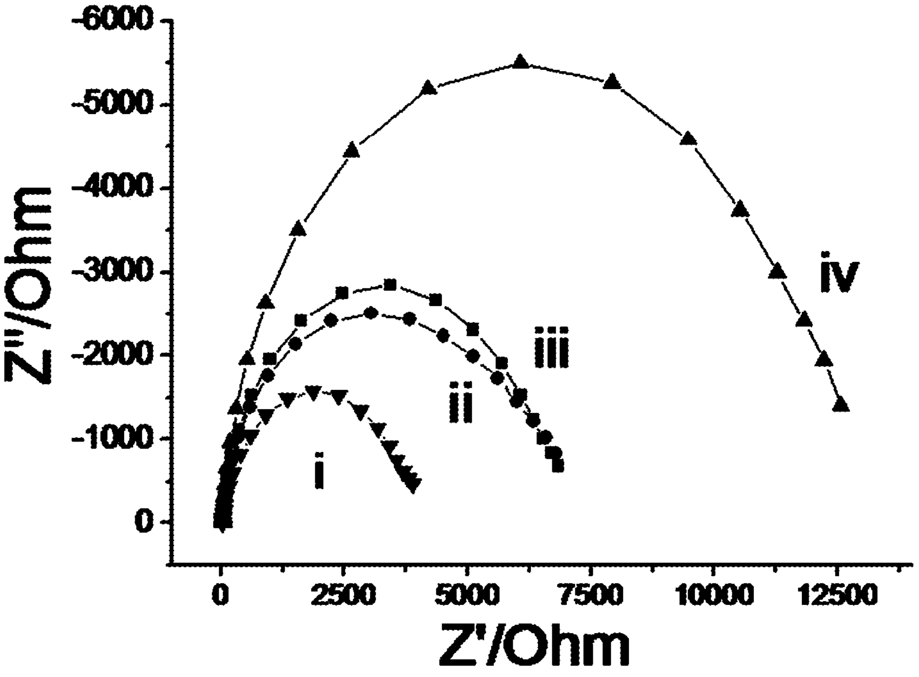
FIG. 7 is a Nyquist plot for (i) bio-BSA/streptavidin/bio anti-HA/'350' at 500 pg/mL (i.e., no yeast-scFv biofragment reagent), (ii) bio-BSA/streptavidin/bio anti-HA/yeast-scFv biofragment (i.e., no antigen), (iii) bio-BSA/streptavidin/bio anti-HA/yeast-scFv biofragment/'Jacob' antigen at 1000 pg/mL, and (iv) bio-BSA/streptavidin/bio anti-HA/yeast-scFv biofragment/'350' antigen at 500 pg/mL complex formation, each determined with a gold coated screen-printed electrode and in 10 mM phosphate buffer solution (pH 7.4) containing 2.5 mM $K_3[Fe(CN)_6]$, 2.5 mM $K_2[Fe(CN)_6]$, and 0.1 M KCl.

The specificity of the immunosensor towards the '350' antigen on the gold coated screen-printed electrode was examined by attempting to capture an antigen that was non-specific to the yeast-scFv biofragment affinity reagent. The 'Jacob' protein was previously shown not to bind with the '350-E2' yeast-scFv clone or with '350-E2'-derived yeast-scFv biofragment. Non-specific binding of the 'Jacob' protein was evaluated by using F-EIS measurements. A high concentration of the 'Jacob' protein (1 ng/mL) was used to determine the detection of background binding (FIG. 7 (ii)). The signals observed for with 'no antigen' case were essentially identical with the 'Jacob' antigen (FIG. 7 (ii) and FIG. 7 (iii)). This indicates that the assay system detects the bulky anti-HA-yeast-scFv biofragment complex, but without significant cross-reaction with the 'Jacob' protein. Comparatively, the $R_{ct}$ increase produced by the target '350' antigen at 500 pg/mL (FIG. 7 (iv)) was much greater. This indicates that yeast-scFv biofragments retain their specificity towards target antigen, which is in accordance with the initial results described above and in Grewal et al., 2013. To assess background noise an assay was performed which excluded the yeast-scFv biofragment layer (FIG. 7 (i)). Non-specific absorption and interaction of the '350' antigen on the bio-BSA/streptavidin/bio-anti-HA screen-printed electrode was examined (FIG. 6 (iii) vs. FIG. 7 (i)), however the $R_{ct}$ signal increase was small, which indicates that non-specific absorption was minimal. The reproducibility of F-EIS measurements for '350' antigen was determined to have a RSD of 4.51% (n=3), while reproducibility of 'Jacob' protein measurements was found to have a RSD of 3.88% (n=3) and reproducibility of 'no antigen' assays was determined to have a RSD of 3.00% (n=3).

Figure 8A:
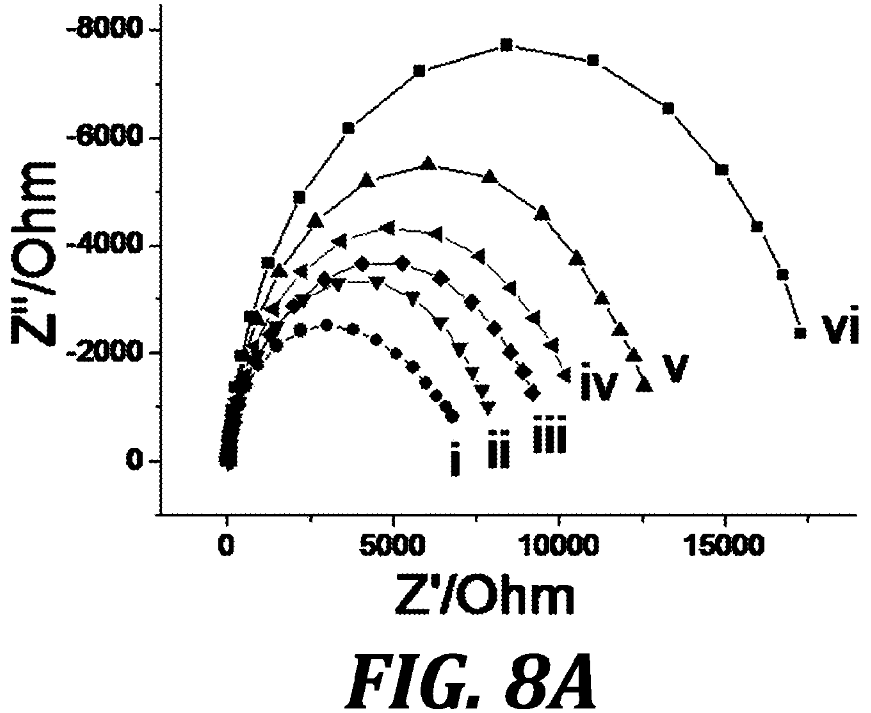
FIG. 8A is a Nyquist plot of the F-EIS responses at the immunosensing surface of a gold coated screen-printed electrode and after incubation with designated concentrations of *E. histolytica* '350' antigen: (i) 0 (ii) 1 pg/mL (iii) 10 pg/mL (iv) 50 pg/mL (v) 500 pg/mL (vi) 1000 pg/mL.
Figure 8B:
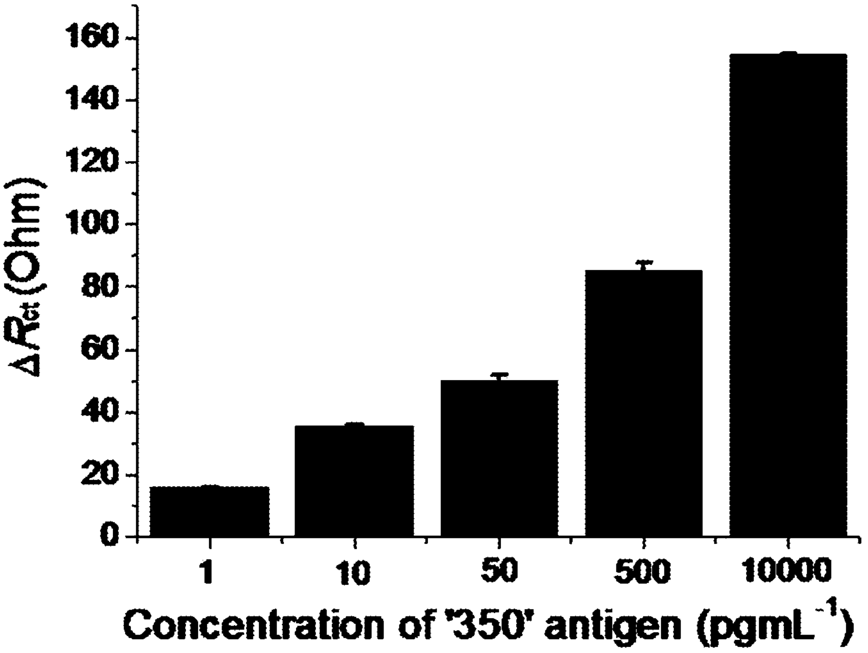
FIG. 8B graphically illustrates the relative change of the charge transfer resistance ($R_{ct}$) responses, normalized to the 'zero-antigen' signal, at the immunosensing surface of a gold coated screen-printed electrode after incubation with designated concentrations of *E. histolytica* '350' antigen. Each data point represents the average of three separate trials (n=3) and error bars represent standard error of measurements within each experiment.

The dynamic range of detection for antigen '350' using yeast-scFv biofragments on the screen-printed electrode was measured before and after the yeast-scFv biofragment modified electrode was incubated with designated concentrations of '350' antigens (1 pg/mL to 1 ng/mL). The $R_{ct}$ signal increased with increasing amounts of antigen concentration (FIG. 8A and FIG. 8B). The presence of antigen detected is accounted by faradaic current generated by $K_3[Fe(CN)6]^{3-}/K_2[Fe(CN)6]^{4-}$ probe. The relative $R_{ct}$ changes corresponding to antigen binding to the yeast-scFv biofragment (FIG. 8B) was calculated as follows:

$$\%\ \text{change of } R_{ct}=\Delta R_{ct}=(R_{ct,\ after}-R_{ct,\ before})/R_{ct,\ before}\times 100 \quad (1)$$

where $R_{ct,\ before}$ was the mean $R_{ct}$ at zero concentration ($R_{ct}$ for bio-BSA/streptavidin/bio anti-HA) and $R_{ct,\ after}$ was the mean $R_{ct}$ at any concentration of the '350' antigen.

The lower limit of detection was confirmed down to 10 pg/mL (588 fM). This concentration of antigen detected is 10 times more sensitive than the lowest detected concentration of '350' antigen on a gold disk electrode, as described above and in Grewal et al., 2013, and about 550 times more sensitive than detecting *E. histolytica* antigen using whole-cell yeast-scFv with fluorescently labeled signal antibodies (Gray, S. A., et al, "Toward Low-Cost Affinity Reagents: Lyophilized Yeast-scFv Probes Specific for Pathogen Antigens," *PLoS ONE* 7: e32042 (2012)). This lower limit of detection is also comparable to the detection of antigen using ELISA and a typical IgG mAb. This increased sensitivity may be attributed in part to the presence of gold particles on the screen-printed electrode surface (the commercially obtained screen printed electrodes uses a gold ink that is cured at 120° C., which forms a rough working surface of gold particles). Gold particles are known for their high electrocatalytic activity allowing for increased sensitivity of biomolecule detection using impedance and other electrochemical measurements. The linear dynamic range of the assay was determined to be from 10 pg/mL (588 fM) to 500 pg/mL (29.4 pM). Reproducibility of the concentrations was each examined on three separate electrodes, resulting in a RSD of <4.1% between the electrodes at each concentration.

Reproducibility of the concentrations was each examined on three separate electrodes, resulting in a RSD of <4.1% between the electrodes at each concentration.

Figure 9A:
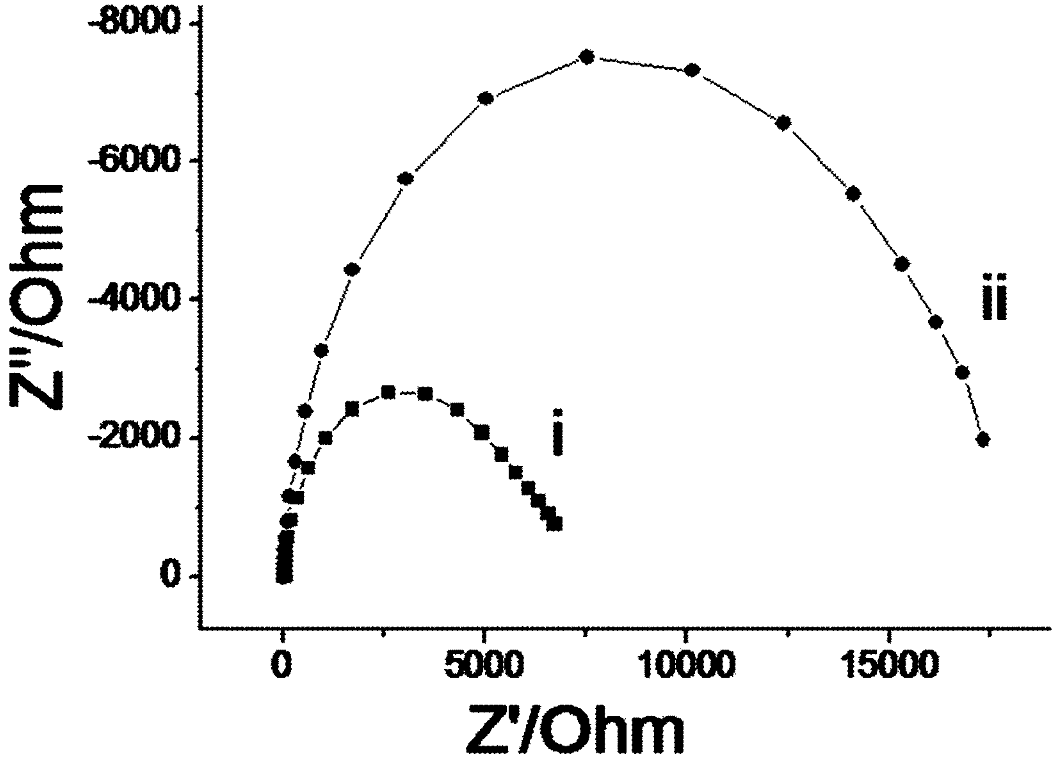
FIG. 9A and FIG. 9B are Nyquist plots for (A) (i) assay with no antigen, (ii) cognate '350' antigen, and (B) (i) assay with no antigen, (ii) cognate '030' antigen in stool, each determined with a gold coated screen-printed electrode and in 10 mM phosphate buffer solution (pH 7.4) containing 2.5 mM $K_3[Fe(CN)_6]$, 2.5 mM $K_2[Fe(CN)_6]$, and 0.1 M KCl. Antigens '350' and '030' concentrations were 500 pg/mL. Stool was diluted ⅕ in PBS.
Figure 9B:
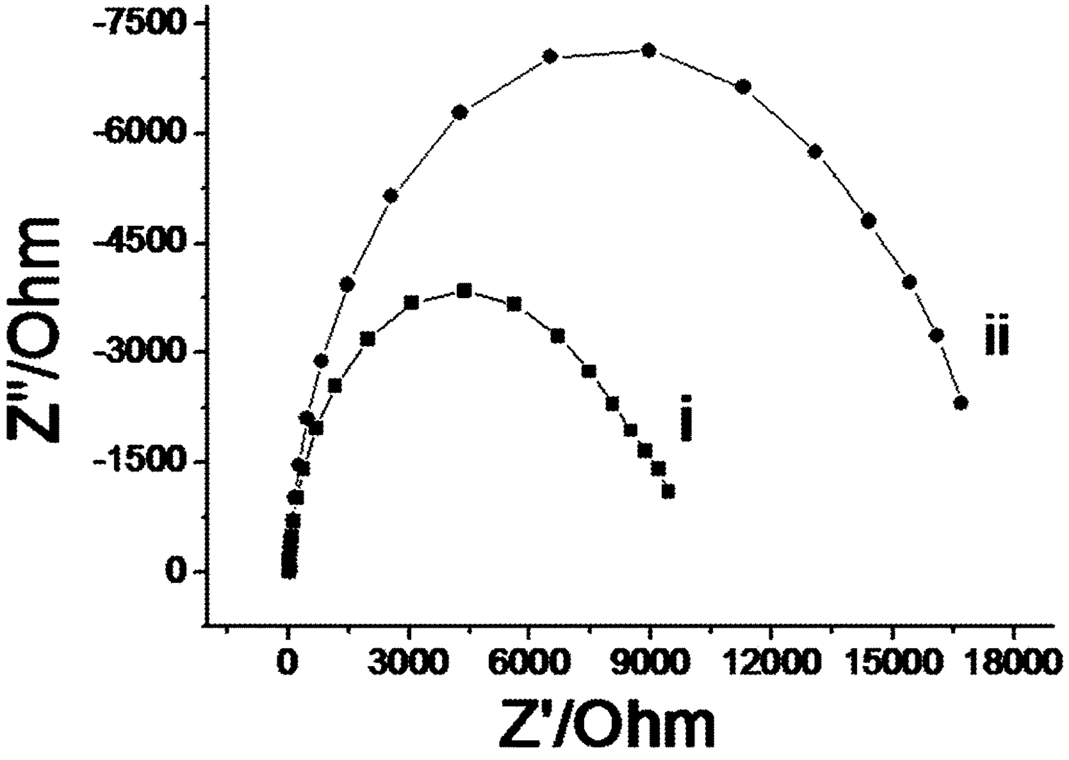
Figure 9C:
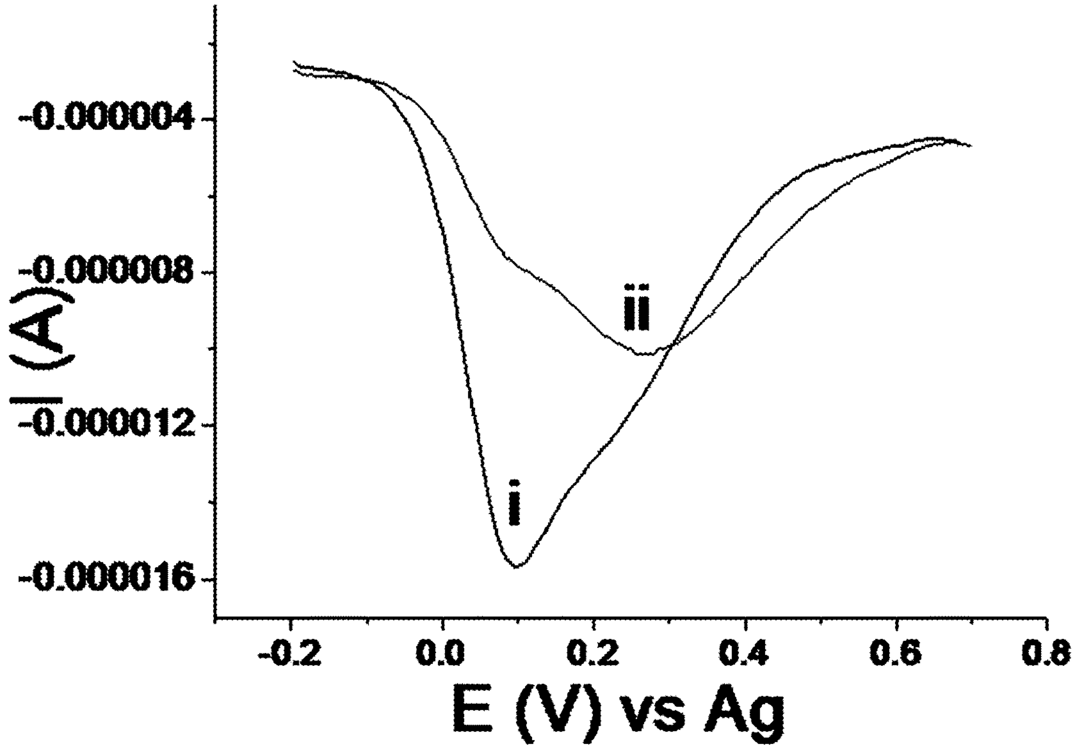
FIG. 9C and FIG. 9D are the DPV responses corresponding to antigen '350' and antigen '030', respectively.
Figure 9D:
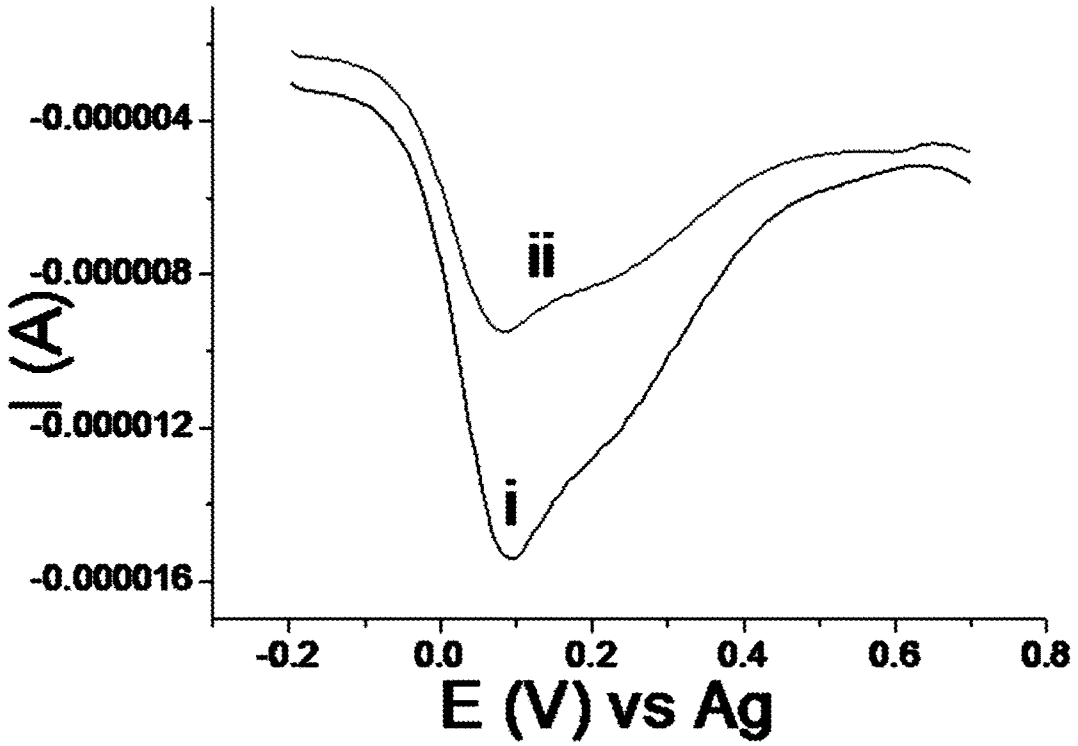

*E. histolytica* cysts are detected in patient stool samples for diagnosis of *E. histolytica* infection. Therefore, the ability to detect cyst antigens in stool matrix is a crucial requirement when designing a clinical diagnostic. Antigens '350' and '030' (each 500 pg/mL) were spiked into a biological matrix comprised of disinfected (for occupational safety) stool diluted ⅕ in PBS. The $R_{ct}$ signal of the assay complex containing the '030-L' yeast-scFv biofragment sensing layer in stool (FIG. 9B (i)), showed a slight increase compared to the '350-E2' yeast-scFv biofragment complex in PBS (FIG. 7 (ii)) and stool (FIGURE A (i)). This signal increase may be attributed to low levels of non-specific adsorption of stool biomolecules on the immunosensor. For both antigens, a clear increase in signal was observed when antigen was spiked into the sample compared to the 'no antigen control' (FIG. 9A and FIG. 9B). The F-EIS measurements were found to have a RSD of 9.88% and 8.45% (n=3) was found for inter-assay signals for antigens '350' and '030', respectively. FIG. 9C and FIG. 9D show the differential pulse profiles, where the current decreases due to increase hindrance of $[Fe(CN)_6]^{3-/4-}$ process. DPV peak current decreased when antigen was captured, compared to the assay complex without antigen (FIG. 9C and FIG. 9D). This is in line with the F-EIS responses (FIG. 9A and FIG. 9B). This indicates that this current diagnostic platform has sufficient specificity to successfully detect antigens, such as from the *E. histolytica* pathogen, in a complex biological matrix. Thus, the biosensor system has demonstrated the potential of yeast-scFv biofragment affinity reagents to detect antigens in clinical samples. A commercial ELISA kit is currently available for *E. histolytica* detection in stool (TechLab *E. histolytica* II test). This diagnostic detects the trophozoite protein Gal/GalNAc lectin, which is different from the presently described target cyst antigens. The commercial TechLab kit uses highly optimized antibodies and has been reported to detect its target antigen at concentrations of ~1000 pg/mL in stool. Thus, the analytical sensitivity of the present system compares favorably to a commercial ELISA functioning in a similar biological matrix, but can be developed and performed much more economically.

Conclusion: In conclusion, it is demonstrated yeast-scFv biofragment affinity reagents can specifically bind to antigens of interest, and can be included into detection assays, including a novel, low-cost system incorporating commercial gold screen-printed electrode for the sensitive detection of antigens in complex samples (e.g., *E. histolytica* antigens in human stool samples). This work is the first demonstration of yeast-scFv biofragments on a portable low-cost platform and the first demonstration of using yeast-scFv biofragment affinity reagents to detect antigens in a complex biological matrix. A new antibody/antigen recognition combination was also demonstrated, consistent with the expectation that new yeast-scFv biofragment affinity reagents can be routinely engineered towards diverse target antigens. Coupling a commercially available battery operated portable potentiostat with the described yeast-scFv biofragment coated screen-printed would allow for field testing of pathogen antigens, such as *E. histolytica* antigens and other antigens that are of clinical interest. Accordingly, the biofragment affinity reagents have the ability to replace mAbs in point of care diagnostics.

The following examples are provided for the purpose of illustrating, not limiting, the invention.

EXAMPLES

Example 1

This Example describes the materials and methods used to generate the illustrative reagents and assays described above for the initial development of a yeast-scFv biofragment probe and related EC bioassay.

Chemicals

All chemicals purchased from the Australian supplier's branch, unless otherwise stated. Lyophilized yeast-scFv, '350', and Jacob antigens were generated at Seattle Biomedical Research Institute, USA. Biotinylated anti-HA obtained from Sapphire Bioscience. Biotinylated BSA was obtained from Thermo Scientific. Streptavidin was obtained from Invitrogen. PBS tablets were obtained from Astral Scientific. Potassium ferrocyanide, potassium ferricyanide, and potassium chloride were obtained from Sigma Aldrich. Protease Inhibitor EDTA-free cocktail tables were obtained from Roche. Glycerol was obtained from Ajax Finechem.

Determination of the Surface Area of the Electrodes

Gold (AU) marcrodisk (diameter=3 mm) working electrodes were purchased from CH Instrument (Austin, USA). Prior to electrochemical experiment, the electrodes were cleaned physically with 0.1 micron alumina, sonicated in acetone for 20 minutes, and chemically with piranha solution ($H_2SO_4$:$H_2O_2$; 3:1) for 30 seconds to remove any organic impurities and finally electrochemically in 0.5 M $H_2SO_4$ until characteristic gold electrode profiles were achieved. The effective working area of the electrodes were determined under linear sweep voltammetric conditions for the one-electron reduction of $K_3[Fe(CN)_6]$ [1.0 mM in water (0.5 M KCl)] and use of the Randles-Sevcik relationship (see A. J. Bard and L. R. Faulkner, Electrochemical Methods: Fundamentals and Applications, John Wiley & Sons, 2000):

$$i_p=0.4463nF(nF/RT)^{1/2}AD^{1/2}v^{1/2}C \quad (1)$$

where $i_p$ is the peak current (A), n (=1) is the number of electrons transferred, A is the effective area of the electrode ($cm^2$), D is the diffusion coefficient of $[Fe(CN)_6]^{3-}$ (taken to be $7.60\times10^{-6}$ $cm^2s^{-1}$), C is the concentration (mol $cm^{-3}$), v is the scan rate ($Vs^{-1}$), and other symbols have their usual meanings.

Generation of Cell-Free Yeast-scFv Biofragments

Whole yeast cells expressing scFv on their surface (whole yeast-scFv), were selected for their binding towards the *E. histolytica* antigen EHI 115350 (Gray, S. A., et al., *PLoS ONE,* 7:e32042 (2012)) called '350' in this report. After confirmation of specific antigen binding, the cells were lyophilized for long-term storage (Gray, S. A., et al., *PLoS ONE,* 7:e32042 (2012)). Lyophilized yeast were disrupted with a mortar and pestle into a fine powder, then 10 mL of PBS, 5% glycerol and protease inhibitor cocktail were added. The sample was centrifuged at 500 rpm for 2 minutes at 15° C. to remove whole yeast. The processed lysates (supernatant) were stored at 4° C. until used.

Dynamic Light Scattering Sizing of Biofragments

To assure that the yeast-scFv fragments were small enough to be useable in the bioassay, DLS measurements (FIG. 2) (Malvern Zetasizer series) were taken of the yeast-scFv biofragments after filtration through a 0.1 μm filter (Millipore). The DLS data confirmed that biofragments existed in the sub 100 nm size range, and lacked detectable whole-cell yeast-scFv.

Assay Protocol

Gold disk electrodes were functionalized with BSA by incubating them for 45 min in biotinylated BSA solution (100 μg/ml) and incubated on a thermoshaker set to 25° C. at 300 rpm. The thermoshaker and these settings (time and temperature) were used in all subsequent steps. The electrodes were washed with 1×PBS (pH 7.4, 137 mM sodium chloride, 2 mM potassium chloride, 10 mM phosphate buffer) after each incubation step. The electrode was incubated in 400 μl of streptavidin (100 ug/ml) solution for 45 minutes. These electrodes were treated with 100 ug/ml of biotinylated HA antibody solution at room temperature for another 45 min, leading to immobilization of the anti-HA on the electrode surface. Finally, the cell-free yeast-scFv biofragment reagent diluted 1/10 in PBS was allowed to react for 45 minutes before washing with PBS. The sensing electrodes were then incubated in 400 μl of antigen solution at varying concentrations to complete the immunoreactions.

Electrochemical Procedure

All electrochemical experiments were conducted at room temperature (25±1° C.) in a standard three-electrode electrochemical cell arrangement using an electrochemical analyzer CHI 650D (CH Instruments, Austin, Tex.), where the electrochemical cell consisted of an Au sensor as a working electrode, a Pt wire counter electrode, and a Ag/AgCl (3 M NaCl) reference electrode. Electrochemical signals were measured in a 10 mM phosphate buffer solution (pH 7.4) containing 2.5 mM $[Fe(CN)_6]^{3-}/[Fe(CN)_6]^{4-}$ (1:1) and 0.1 M KCl. Differential pulse voltammetric (DPV) signals were obtained with a potential step of 5 mV, pulse amplitude of 50 mV, pulse with 50 ms, and a pulse period of 100 ms. The EIS spectra were recorded in 10 mM phosphate buffer solution (pH 7.4) containing 2.5 mM $[Fe(CN)_6]^{3-}/[Fe(CN)_6]^{4-}$ (1:1) and 0.1 M KCl using an alternating current voltage of 10 mV, with the frequency range of 0.1 Hz-100 kHz.

The faradaic current generated by the $K_3[Fe(CN)_6]/K_2[Fe(CN)_6]$ probe accounts on the presence of a protein. The current changes corresponding to target antigen binding to the antibody was calculated as follows:

$$\%\ \text{Decrease of peak current}=(I_{before}-I_{after})/I_{before}\times 100 \qquad (2)$$

where $I_{before}$=mean current at zero target concentration (e.g., current generated by the bio-BSA/streptavidin/bio-anti-HA/yeast-scFv layer), $I_{after}$=mean current at any concentration of target antigen.

Example 2

This Example describes the materials and methods used to generate the illustrative reagents and assays described above for the subsequent development of yeast-scFv biofragment probes and the related EC bioassay incorporating screen-printed electrodes.

Chemicals and Materials

All chemicals purchased from the Australian supplier's branch, unless otherwise stated. Stool samples, lyophilized yeast-scFv, and *E. histolytica* antigens EHI 115350, EHI 182030, and EHI 044550 (called '350', '030', and 'Jacob' respectively) in this report were produced by The University of Washington, USA and Seattle Structural Genomics Center for Infectious Disease (SSGCID). Biotinylated anti-HA antibody (Bio-anti-HA) was purchased from Sapphire Bioscience. Biotinylated bovine serum albumin (BSA) was obtained from Thermo Scientific. Streptavidin was procured from Invitrogen. Phosphate buffered saline (PBS) tablets were purchased from Astral Scientific. Potassium ferrocyanide, potassium ferricyanide, and potassium chloride were all purchased from Sigma Aldrich. Protease Inhibitor EDTA-free cocktail tablets were obtained from Roche. Glycerol was procured from Ajax Finechem. Screen-printed gold electrodes, DRP-C220BT (geometric area=0.126 $cm^2$), were acquired from Dropsens, Spain. Millex-VV 0.1 μm, Durapore PVDF (diameter 33 mm), low protein binding syringe filters were purchased from Millipore. The effective working area (=0.180 $cm^2$) of the screen-printed gold electrodes were determined under linear sweep voltammetric conditions for the one-electron reduction of $K_3[Fe(CN)_6]$ [1.0 mM in water (0.5 M KCl)] and use of the Randles-Sevcik relationship (Bard and Faulkner, 2000; Grewal et al., 2013).

Residues 135-271 of antigen EHI 115350 ('350) were expressed recombinantly in *E. coli* in a modified, N-terminal 6×His pET11b vector and purified by Ni-NTA IMAC. Residues 159-481 of EHI 044550 ('Jacob') were expressed in a pE-SUMO vector (Life Sensors), also purified by Ni-NTA IMAC, and cleaved from the His-SUMO tag by SUMO protease digestion. Full-length EHI 182030 ('030') was expressed in *E. coli* and purified in Tier 1 of SSGCID (Bryan et al., "High-throughput protein production and purification at the Seattle Structural Genomics Center for Infectious Disease," *Acta Crystallograph. Sect. F Struct. Biol. Cryst. Commun.* 67:1010-1014 (2011); Stacy et al., "Structural genomics of infectious disease drug targets: the SSGCID," *Acta Crystallograph. Sect. F Struct. Biol. Cryst. Commun.* 6:979-984. (2011)).

The yeast-scFv library was a generous gift from K. Dane Wittrup. Antigens 350 and 030 were biotinylated with EZ-Link NHS-PEG4 biotin (Thermo Pierce), respectively. Yeast selections were conducted as before (Chao et al., "Isolating and engineering human antibodies using yeast surface display," *Nat. Protoc.* 1:755-768 (2006); Gray et al., 2012). In brief, two rounds of magnetic selection were conducted on the induced library with 100 nM of a biotinylated antigen and streptavidin (R1)- or α-biotin(R2)-conjugated beads (Milentyi). The resultant output was further enriched for bio-antigen/SA-PE and α-myc-FITC double-positive cells through two rounds on a Beckman Aria II cell sorter. After plating, individual clones were confirmed to be antigen specific by flow cytometry analysis, and clone diversity was determined by scFv PCR amplification and BstNI digest (New England Biosciences, USA).

The stool matrix was derived from human samples collected by the International Centre for Diarrheal Disease Research, Bangladesh (ICDDR,B) with institutional review board approval from the University of Washington and the ICDDR,B. Five 1-2 mL *E. histolytica*-negative samples were combined, diluted 1:1 in PBS, and spun at high speed for 5 minutes. The supernatant was collected and disinfected by boiling for 10 minutes at 90° C. Before use, disinfection was confirmed by 3 days absence of microbial growth on tryptic soy and nutrient agar plates.

Generation of Yeast-scFv Biofragments

After confirmation of specific antigen binding, the cells were lyophilized for long-term storage as described (Gray et al., 2012), following a modified protocol that added 10% dextran and 5% sodium glutamate to yeast. Yeast-scFv biofragments were created as described above and in Grewal et al., 2013, with a modified protocol that added sodium azide. Briefly, lyophilized yeast was disrupted with a mortar and pestle into a fine powder, then 10 mL of PBS, 5% glycerol and protease inhibitor cocktail were added. The sample was centrifuged at 500 RCF for 2 minutes at 15° C. to remove whole yeast. To prevent microbial growth, sodium azide 0.05% was added. The processed lysates (supernatant) were stored at 4° C. until use and filtered using a 0.1 μm filter.

Assay Protocol

Screen-printed gold electrodes were functionalized with BSA by incubating them in 700 μl of biotinylated BSA solution (500 μg/mL) for 1 hour at 25° C. on an intelli-mixer (PCOD Scientific) with gentle agitation. These intelli-mixer settings were used in all subsequent steps. The electrodes were then stored overnight at 4° C. The electrodes were then washed with 1×PBS (pH 7.4, 137 mM sodium chloride, 2 mM potassium chloride, 10 mM phosphate buffer) after each incubation step. The electrode was incubated in 700 μL of streptavidin (500 μg/mL). These functionalized electrodes were then treated with 100 μg/mL of biotinylated HA antibody solution at room temperature for another hour, leading to immobilization of the anti-HA antibody on the electrode surface. Finally, the yeast-scFv biofragment reagent diluted ⅕ in PBS was allowed to bind (by virtue of the interaction between anti-HA and the HA affinity tag cloned into the yeast-display scFv) for 1 hour before washing with PBS. This step tethered the yeast-scFv biofragment to the electrode surface while at the same time removing yeast fragments that do not bear displayed scFv. The electrodes were then incubated in 700 μL of antigen solution (spiked in either PBS or stool) at varying concentrations to complete the immunoreactions.

Electrochemical Procedure

All electrochemical experiments were conducted at room temperature (25±1° C.) using screen-printed gold electrodes which comprised of an Ag reference, gold counter, and a 4 mm diameter gold working electrode using an electrochemical analyser CHI 650D (CH Instruments, Austin, Tex.). Electrochemical measurements were measured in a 10 mM phosphate buffer solution (pH 7.4) containing 2.5 mM $[Fe(CN)6]^{3-}/[Fe(CN)6]^{4-}$ (1:1) and 0.1 M KCl. Differential pulse voltammetric (DPV) signals were obtained with a potential step of 5 mV, pulse amplitude of 50 mV, pulse width 50 ms, and a pulse period of 100 ms. The EIS spectra were recorded using an alternating current voltage of 10 mV, with the frequency range of 1 Hz-100 kHz.

While illustrative embodiments have been illustrated and described, it will be appreciated that various changes can be made therein without departing from the spirit and scope of the invention.

The invention claimed is:

1. A composition for selectively binding an antigen of interest in a sample, the composition comprising a cell wall fragment immobilized to a conductive or semi-conductive electrode surface by an intervening tether construct, wherein the cell wall fragment displays at least one heterologous antigen-binding molecule and is a fragment of a yeast cell wall, a bacterium cell wall, or a plant cell wall;

wherein the cell wall fragment is less than 200 nm at its greatest dimension; and wherein the at least one heterologous antigen-binding molecule is an antibody, an antigen-binding antibody fragment, or a T-cell receptor (TCR) that selectively binds the antigen of interest.

2. The composition of claim 1, wherein the yeast is from the genus *Saccharomyces* or *Pichia.*

3. The composition of claim 1, wherein the antibody or antigen-binding antibody fragment is a single-chain antibody, a bispecific antibody, a Fab fragment, or a $F(ab)_2$ fragment.

4. The composition of claim 3, wherein the single-chain antibody is a single-chain variable fragment (scFv), single-chain Fab fragment (scFab), a single variable domain on a heavy-chain antibody fragment ($V_H$H fragment), a variable domain of new antigen receptor fragment ($V_{NAR}$ fragment), or single domain antibody.

5. The composition of claim 1, wherein the conductive or semi-conductive electrode surface is substantially free of cell wall fragments not displaying the at least one heterologous antigen-binding molecule.

6. The composition of claim 1, wherein the cell wall fragment is produced by disruption of the cell wall.

7. The composition of claim 6, wherein the at least one heterologous antigen-binding molecule is attached to the cell wall surface prior to disruption of the surface by inducing expression and translocation of the molecule to, or assembly of the molecule on, the interior or exterior cell wall surface.

8. A method of detecting the presence of an antigen of interest in a biological sample, comprising:

1) acting a biological sample with the composition of claim 1 under conditions sufficient to permit the binding of the heterologous antigen-binding molecule with the antigen of interest to form a complex; and
2) detecting formation of the complex.

9. The method of claim 8, further comprising contacting the complex with a detection reagent that binds to the antigen of interest.

10. The method of claim 9, wherein the detection reagent comprises a detectably-labeled reporter reagent, and the method further comprises separating the unbound detectably labeled-reporter from the composition.

11. The method of claim 8, further comprising contacting the immobilized antigen of interest with an electroactive molecule and measuring electron transfer resistance at the electrode surface, wherein binding of the antigen of interest to the composition is detected by a change in the electron transfer resistance as compared to the electron transfer resistance when the antigen of interest is not present.

12. The method of claim 9, wherein the biological sample is selected from the group consisting of blood, urine, sputum, mucus, saliva, cerebral spinal fluid, tissues, stool, nutrient sources, or processed derivatives thereof.

13. The method of claim 11, wherein the electroactive molecule is a redox probe.

14. The method of claim 13, wherein the redox probe is $[Fe(CN)_6]^{3-/4-}$.

15. An antigen detection system, comprising:

the composition of claim 1, an electroactive molecule, and a device to monitor electric current, electric potential, and/or electric impedance.

16. The system of claim 15, wherein the electrode surface is on a screen-printed gold electrode.

17. The system of claim 15, wherein the electroactive molecule is a redox probe.

18. The system of claim 15, wherein the intervening tether construct is an epitope-tag binding molecule that binds to an epitope tag present in the heterologous antigen-binding molecule of the composition.

19. The system of claim 17, wherein the redox probe is $[Fe(CN)_6]^{3-/4-}$.

* * * * *